US011530313B2

(12) United States Patent
Rentsch et al.

(10) Patent No.: US 11,530,313 B2
(45) Date of Patent: Dec. 20, 2022

(54) PROCESS OF CONTROLLED CHEMICAL REACTION OF A SOLID FILLER MATERIAL SURFACE AND ADDITIVES TO PRODUCE A SURFACE TREATED FILLER MATERIAL PRODUCT

(71) Applicant: OMYA INTERNATIONAL AG, Oftringen (CH)

(72) Inventors: Samuel Rentsch, Aarburg (CH); Matthias Buri, Rothrist (CH); René Vinzenz Blum, St. Urban (CH); Martin Brunner, Wallbach (CH); Patrick A. C. Gane, Rothrist (CH)

(73) Assignee: OMYA INTERNATIONAL AG, Oftringen (CH)

( * ) Notice: Subject to any disclaimer, the term of this patent is extended or adjusted under 35 U.S.C. 154(b) by 0 days.

(21) Appl. No.: 16/862,483

(22) Filed: Apr. 29, 2020

(65) Prior Publication Data

US 2021/0079196 A1 Mar. 18, 2021

Related U.S. Application Data

(63) Continuation of application No. 14/431,345, filed as application No. PCT/EP2013/071185 on Oct. 10, 2013, now abandoned.

(30) Foreign Application Priority Data

Oct. 16, 2012 (EP) .................................... 12188739

(51) Int. Cl.
*C08K 9/04* (2006.01)
*C09C 1/02* (2006.01)
(Continued)

(52) U.S. Cl.
CPC .............. *C08K 9/04* (2013.01); *C07D 307/60* (2013.01); *C09C 1/021* (2013.01); *D01F 1/02* (2013.01);
(Continued)

(58) Field of Classification Search
CPC .................................. C08K 9/04; C09C 1/021
See application file for complete search history.

(56) References Cited

U.S. PATENT DOCUMENTS 3,926,873 A 12/1975 Aishima
4,328,041 A 5/1982 Wilson
(Continued)

FOREIGN PATENT DOCUMENTS

EP 0325114 A2 7/1989
EP 2371766 A1 10/2011
(Continued)

OTHER PUBLICATIONS

Hu et al. "Siperhydrophobic Surface Fabricated from Fatty Acid-Modified Precipitated Calcium Carbonate." Ind. Eng. Chem. Res. 2010, 49, pp. 5625-5630.
(Continued)

*Primary Examiner* — Peter Y Choi
(74) *Attorney, Agent, or Firm* — ALGM LLP; Harry J. Guttman

(57) ABSTRACT

The present invention relates to a process for preparing a surface treated filler material product with succinic anhydride(s), a surface treated filler material product, a polymer composition, a fiber and/or filament and/or film and/or thread comprising the surface treated filler material product and/or the polymer composition, an article comprising the surface treated filler material product and/or the polymer composition and/or the fiber and/or filament and/or film and/or thread as well as the use of a mono-substituted
(Continued)

succinic anhydride for decreasing the hydrophilicity of a calcium carbonate-containing filler material surface and the use of a surface-treated filler material product for initiating the crosslinking reaction in epoxide resins.

36 Claims, 2 Drawing Sheets

Related U.S. Application Data

(60) Provisional application No. 61/717,135, filed on Oct. 23, 2012.

(51) Int. Cl.
 *C07D 307/60* (2006.01)
 *D01F 1/02* (2006.01)
 *D04H 3/007* (2012.01)

(52) U.S. Cl.
 CPC ......... *D04H 3/007* (2013.01); *C01P 2004/61* (2013.01); *C01P 2004/62* (2013.01); *C01P 2006/12* (2013.01); *D10B 2321/022* (2013.01); *D10B 2501/00* (2013.01); *D10B 2505/04* (2013.01); *D10B 2509/00* (2013.01); *Y10T 442/60* (2015.04)

(56) References Cited

U.S. PATENT DOCUMENTS

| | | | |
|---|---|---|---|
| 4,359,556 | A | 11/1982 | Lakshmanan et al. |
| 4,407,986 | A | 10/1983 | Nomura et al. |
| 4,520,073 | A | 5/1985 | Randolph et al. |
| 4,876,152 | A | 10/1989 | Kang |
| 5,135,967 | A | 8/1992 | Aumann et al. |
| 7,341,704 | B2 | 3/2008 | Kasahara |
| 7,507,561 | B2 | 3/2009 | Ramakrishna et al. |
| 9,012,554 | B2 | 4/2015 | Saunders |
| 2002/0102404 | A1 | 8/2002 | Nakai et al. |
| 2004/0162376 | A1 | 8/2004 | Blanchard et al. |
| 2006/0020056 | A1 | 1/2006 | Dombrowski et al. |
| 2006/0148930 | A1 | 7/2006 | Blanchard et al. |
| 2007/0213434 | A1 | 9/2007 | Lima |
| 2007/0256598 | A1 | 11/2007 | Blanchard et al. |
| 2009/0227721 | A1 | 9/2009 | Blanchard et al. |
| 2009/0324979 | A1 | 12/2009 | Roussel |
| 2011/0100575 | A1 | 5/2011 | Schmidt-Thuemmes et al. |
| 2011/0245396 | A1 | 10/2011 | Blanchard et al. |
| 2012/0288650 | A1 | 11/2012 | Freese et al. |
| 2014/0134380 | A1 | 5/2014 | Yoon et al. |
| 2015/0240056 | A1 | 8/2015 | Rentsch et al. |

FOREIGN PATENT DOCUMENTS

| | | |
|---|---|---|
| EP | 2447213 A1 | 5/2012 |
| EP | 2524898 A1 | 11/2012 |
| EP | 2554358 A1 | 2/2013 |
| EP | 2607399 A1 | 6/2013 |
| EP | 2840065 A1 | 2/2015 |
| GB | 2336366 A | 10/1999 |
| JP | 54162746 | 12/1979 |
| JP | 11060928 A | 3/1999 |
| KR | 2010/0108683 A | 10/2010 |
| RU | 2345189 C2 | 1/2009 |
| RU | 2448906 C2 | 4/2012 |
| WO | 9202587 A1 | 2/1992 |
| WO | 95/20615 A1 | 8/1995 |
| WO | 97/47670 A1 | 12/1997 |
| WO | 9961521 A1 | 12/1999 |
| WO | 0020336 A1 | 4/2000 |
| WO | 0132787 A1 | 5/2001 |
| WO | 03082966 A1 | 10/2003 |
| WO | 2004/057008 A1 | 7/2004 |
| WO | 2007110611 A1 | 10/2007 |
| WO | 2008077156 A2 | 6/2008 |
| WO | 2010/001268 A2 | 1/2010 |
| WO | 2011124564 A1 | 10/2011 |
| WO | 2011/147778 A1 | 12/2011 |
| WO | 2012/018327 A1 | 2/2012 |
| WO | 2012/094758 A1 | 7/2012 |
| WO | 2013/142473 A1 | 9/2013 |
| WO | 2013/169174 A1 | 11/2013 |
| WO | 2013/190274 A2 | 12/2013 |
| WO | 2014/060286 A1 | 4/2014 |
| WO | 2015/185533 A1 | 12/2015 |
| WO | 2016/087286 A1 | 6/2016 |

OTHER PUBLICATIONS

The International Search Report dated Nov. 20, 2013 for PCT Application No. PCT/EP2013/071185.
The Written Opinion of the International Searching Authority dated Nov. 20, 2013 for PCT Application No. PCT/EP2013/071185.
Octadecenysuccinic anhydride from www.buyersguidechem.com. (Year: 2019).
Tabtiang, A., et al., "The performance of selected unsaturated coatings for calcium carbonate filler in polypropylene," European Polymer Journal 36 (2000) 137-148.
The International Search Report dated Sep. 5, 2017 from PCT/EP2017/067674.
The Written Opinion of the International Searching Authority dated Sep. 5, 2017 from PCT/EP2017/067674.
Kim, Mechanical Properties and Thermal Stability of Poly(L-lactide)/Calcium Carbonate Composites, Journal of Applied Polymer Science, 109, 2008, pp. 3087-3092.
Nekhamanurak, The influence of micro-/nano-CaCO3 on thermal stability and metl rheology behavior of poly(lactic acid), Energy Procedia, 56, 2014, pp. 118-128.
Coogle Patents translation of JP 11-060928 (1999, 8 pages).
RU2345189C2 (Jan. 27, 2009)—English-language abstract from Espacenet, 1 page.
RU2448906C2 (Apr. 27, 2012)—English-language abstract from Espacenet, 1 page.
NonFinal Office action in U.S. Appl. No. 16/305,499 dated Oct. 20, 2020, 17 pages.
Response to nonFinal Office action in U.S. Appl. No. 16/305,499 dated Feb. 2, 2021, 15 pages.
Final Office action in U.S. Appl. No. 16/305,499 dated Apr. 23, 2021, 15 pages.
Response to Final Office action in U.S. Appl. No. 16/305,499 dated Oct. 13, 2021, 16 pages.
NonFinal Office action in U.S. Appl. No. 16/305,499 dated Oct. 20, 2021, 17 pages.
Response to nonFinal Office action in U.S. Appl. No. 16/305,499 dated Jan. 31, 2022, 16 pages.
Final Office action in U.S. Appl. No. 16/305,499 dated Feb. 14, 2022, 19 pages.

PROCESS OF CONTROLLED CHEMICAL REACTION OF A SOLID FILLER MATERIAL SURFACE AND ADDITIVES TO PRODUCE A SURFACE TREATED FILLER MATERIAL PRODUCT

The present invention relates to a process for preparing a surface treated filler material product with succinic anhydride(s), a surface treated filler material product, a polymer composition, a fiber and/or filament and/or film and/or thread comprising the surface treated filler material product and/or the polymer composition, an article comprising the surface treated filler material product and/or the polymer composition and/or the fiber and/or filament and/or film and/or thread as well as the use of a mono-substituted succinic anhydride for decreasing the hydrophilicity of a calcium carbonate-containing filler material surface and the use of a surface-treated filler material product for initiating the crosslinking reaction in epoxide resins.

In practice, filler materials and especially calcium carbonate-containing filler materials are often used as particulate fillers in thermoplastic polymer products, like fibers, filaments, films and/or threads, usually made of polyethylene (PE), polypropylene (PP), polyurethane (PU), polyvinylchloride (PVC), polyester (PES) and/or polyamide (PA). However, additives are introduced to provide the filler material with a coating and to improve the dispersability of said mineral filler material in the polymer composition as well as possibly to improve the processability of this polymer composition and/or properties of the final application products such as fibers, filaments, films and/or threads. An elimination of such additives would unacceptably reduce the resulting fiber, filament, film and/or thread quality. Furthermore, it is to be noted that such mineral filler materials are generally associated with the presence of volatiles evolving at temperatures reached during the application of such mineral fillers and/or in the processing of said polymer products comprising such mineral fillers. Such volatiles may, for example, be:

- inherently associated with the mineral filler ("inherent volatiles"), and is especially associated water, and/or
- introduced during the treatment of the mineral filler ("added volatiles"), for example, to render the mineral filler more dispersible within a polymeric plastic medium, and/or
- generated by the reaction of inherent organic materials and/or added organic materials, with the mineral filler; such reactions may especially be induced or enhanced by temperatures reached during the introduction and/or processing of the polymeric material comprising the mineral filler, such as during extrusion or compounding processes; and/or
- generated by the degradation of inherent organic materials and/or added organic materials, forming $CO_2$, water and possibly low molecular mass fractions of these organic materials; such a degradation may especially be induced or enhanced by temperatures reached during the introduction and/or processing of the polymeric material comprising the mineral filler, such as during extrusion or compounding processes.

As a result of the presence of such volatiles, it may be difficult to prepare a fiber, filament, film and/or thread free of voids leading to uneven surfaces and thus to a degradation of the quality of the final polymer product comprising such filler material. Moreover, volatiles may lead to a reduction in the tensile and tear strength of such a fiber, filament, films and/or threads, and may degrade its visible aspects, in particular of its visible uniformity. Furthermore, volatiles can generate excessive foaming of the mineral filled polymer melt during a step of compounding, causing unwanted product build-up at the vacuum extraction and hence, forcing a reduced output rate.

In the art, several attempts have been made to improve the applicability of mineral filler materials and especially calcium carbonate-containing mineral filler materials, e.g. by treating such mineral filler materials with aliphatic carboxylic acids, and aliphatic carboxylic acid salts, which in some cases may also be referred to as fatty acids and fatty acid salts. For instance, WO 00/20336 relates to an ultrafine natural calcium carbonate, which may optionally be treated with one or several fatty acids or one or several salts or mixtures thereof, and which is used as a rheology regulator for polymer compositions.

Likewise, U.S. Pat. No. 4,407,986 relates a precipitated calcium carbonate that is surface-treated with a dispersant that may include higher aliphatic acids and their metal salts in order to limit the addition of lubricant additives when kneading this calcium carbonate with crystalline polypropylene and to avoid the formation of calcium carbonate aggregates that limit the impact strength of the polypropylene.

EP 0 998 522 relates to surface treated calcium carbonate filler for breathable films using fatty acids of at least 10 carbon atoms wherein the filler before and after the treatment process has to be mostly free of moisture in the range of below 0.1 wt.-%.

However, to achieve and maintain such low moisture content, a high consumption of energy and costs is required. Thus, such low moisture content is not the ideal parameter for influencing and controlling the reaction of a solid mineral surface with treatment additives to achieve a good quality of surface treated filler material product at low energy costs.

DeArmitt et al., Improved thermoplastic composites by optimised surface treatment of the mineral fillers, Institute for Surface Chemistry, August 2000, describes a wet treatment process in which a batch suspension comprising a mineral filler material is contacted with a dispersant at room temperature for one hour. However, such wet treatment process has the disadvantage that the wetting of a dry product for treatment and the subsequent drying is energy- and cost-consuming.

In EP 0 325 114, relating to non-sagging underseal compositions for motor vehicles based on polyvinyl chloride which has improved rheological and adhesion properties, Example 7 discloses a mixture of an ammonium salt of 12-hydroxystearic acid in combination with a fatty acid (in a weight ratio of 1:1) used to treat a mineral filler.

WO 03/082966 relates to a cross-linkable and/or cross-linked nanofiller composition which, in optional embodiments, may additionally include fillers that may or may not be coated with stearic acid, stearate, silane, siloxane and/or titanate. Such nanofiller compositions are used to increase barrier properties, strength and heat distortion temperatures, making them useful in medical, automotive, electrical, construction and food application.

US 2002/0102404 describes dispersible calcium carbonate particles coated on their surface with a combination of saturated and unsaturated aliphatic carboxylic acids and salts thereof along with an organic compound such as a phthalic ester, which are used in adhesive compositions to improve viscosity stability and adhesion properties.

Moreover, US 2002/0102404 requires the implementation of a mixture of saturated and unsaturated aliphatic carboxylic acids/salts. The presence of unsaturated aliphatic carboxylic acids/salts increases the risk of unwanted in situ side reactions with the double bond during processing of any unsaturated aliphatic carboxylic acid/salt-comprising material. Additionally, the presence of unsaturated aliphatic carboxylic acids/salts may result in discoloration of, or unwanted odour development, and notably rancid odours, in the material in which they are implemented.

Claim 11 of WO 92/02587 indicates that a saponified sodium salt solution of at least one high molecular weight unsaturated fatty acid or combination of at least one high molecular weight unsaturated fatty acid and at least one high molecular weight unsaturated fatty acid, may be added to a pre-heated slurry of precipitated calcium carbonate, to ultimately produce a desired level of fatty acid coating on the calcium carbonate before proceeding with further process steps.

The abstract of JP54162746 discloses a composition comprising given relative amounts of rigid vinyl chloride resin, fatty acid treated-colloidal calcium carbonate, and barium stearate used in order to improve the heat stability of the vinyl chloride composition.

U.S. Pat. No. 4,520,073 describes mineral filler materials with improved hydrophobic coatings prepared by pressure coating of porous minerals using steam as a carrier for the coating material. Said coating material may be selected, among other options, from long chain aliphatic fatty acids and their salts.

WO 01/32787 describes a particulate alkaline earth metal carbonate material product which has on its particles a coating of hydrophobic material comprising a composition formed of (a) a first component which comprises the reaction product of the alkaline earth metal carbonate and at least one given aliphatic carboxylic acid and (b) a second component having a carbonate release temperature substantially higher than the first component comprises a compound of formula $CH_3(CH_2)_m COOR$.

WO 2008/077156 A2 relates to spunlaid fibers comprising at least one polymeric resin and at least one filler having an average particle size of less than or equal to about 5 microns and/or having a top cut of less than about 15 microns, wherein the at least one filler is present in an amount of less than about 40% by weight, relative to the total weight of the spunlaid fibers. The coating of the filler is described as being at least one organic material chosen from fatty acids and salts and esters thereof, e.g. stearic acid, stearate, ammonium stearate and calcium stearate.

GB 2 336 366 A relates to filled thermoplastic compositions, and, in particular, filled low density polyethylene compositions which are to be formed into products or articles by the process of extrusion. It is further described that the hydrophobising agent is preferably an organic carboxylic acid or partially or fully neutralised salt thereof which has at least one saturated or unsaturated hydrocarbon chain having from 8 to 28 carbon atoms, if the particulate mineral filler has a neutral to alkaline surface reaction, for example calcium carbonate.

However, the prior art does rarely disclose surface treated mineral filler materials that are suitable for polymer compositions and which would solve the following multifaceted technical problem:
to prepare a surface treated filler material such that it is sufficiently hydrophobic for fibers, filaments and/or films and/or thread applications;
to prepare a surface treated filler material having a low moisture pick up susceptibility such that the moisture adsorption is e.g. of ≤0.8 mg/g;
to prepare a surface treated filler material featuring an increased volatile onset temperature;
to prepare a surface treated filler material featuring a limited total quantity of volatiles evolved between 25° C. and 350° C.;
to prepare a surface treated filler material by using a surface treatment agent featuring a workable viscosity, that is to say a viscosity of less than 1.000 mPa·s at 20° C.;
to identify a surface treatment agent featuring at least an equal flash point than an aliphatic carboxylic acid comprising the same alkyl substituent such that the safety requirements during surface treatment under heat exposure are not increased and/or the safety risks at equal treatment temperature are about the same;
to identify a surface treatment agent that achieves the above regardless of whether or not the at least one surface treated filler material undergoes a salt exchange on contact with the surface treatment agent to create corresponding calcium salts on the surface of the surface treated filler material;
the fibers, filaments, films and threads comprising such mineral filler material show good mechanical properties such as tensile modulus, tensile test at yield and at break, elongation at break and tear resistance.

Thus, there is still a need for providing processes for preparing surface treated filler material products which address the foregoing technical problems described and especially allows for preparing surface treated calcium carbonate-containing mineral filler materials for improving the mechanical properties of final application products such as fibers, filaments, films and threads comprising such surface treated filler material products.

Accordingly, it is an objective of the present invention to provide a process for preparing a surface treated filler material product having improved surface characteristics, and especially a low hydrophilicity. A further objective is to provide a process for preparing a surface treated filler material product featuring low moisture pick up susceptibility. Even a further objective is to provide a process for preparing a surface treated filler material product having a high volatile onset temperature. A still further objective is to provide a process for preparing a surface treated filler material product featuring a limited quantity of total volatiles evolved at temperatures of between 25 and 350° C. A further objective is to provide a process for preparing a surface treated filler material product by using a surface treatment agent which can be easily handled and features a high flash point. A further objective is to provide a process for preparing a surface treated filler material product that can be carried out under cost-efficient and mild conditions, i.e. by avoiding an intensive thermal treatment. Further objectives can be gathered from the following description of the invention.

The foregoing and other objectives are solved by the subject-matter as defined herein in claim 1.

Advantageous embodiments of the inventive a process for preparing a surface treated filler material product are defined in the corresponding sub-claims.

According to one aspect of the present application a process for preparing a surface treated filler material product with succinic anhydride(s) is provided, the process comprising at least the steps of:
a) providing at least one calcium carbonate-containing filler material having
   i) a weight median particle size $d_{50}$ value in the range from 0.1 μm to 7 μm, ii) a top cut $(d_{98}) \leq 15$ μm, iii) a specific surface area (BET) of from 0.5 to 150 m²/g as measured by the BET nitrogen method, and iv) a residual total moisture content of from 0.01 to 1 wt.-%, based on the total dry weight of the at least one calcium carbonate-containing filler material, b) providing at least one mono-substituted succinic anhydride and optionally at least one mono-substituted succinic acid in an amount of from 0.1 to 3 wt.-%, based on the total dry weight of the at least one calcium carbonate-containing filler material of step a), c) contacting the surface of the at least one calcium carbonate-containing filler material of step a) under mixing, in one or more steps, with the at least one mono-substituted succinic anhydride and the optional at least one mono-substituted succinic acid of step b) such that a treatment layer comprising the at least one mono-substituted succinic anhydride and the optional at least one mono-substituted succinic acid and/or salty reaction product(s) thereof is formed on the surface of said at least one calcium carbonate-containing filler material of step a), wherein the temperature before and/or during contacting step c) is adjusted such that the temperature is at least 2° C. above the melting point of the at least one mono-substituted succinic anhydride and the optional at least one mono-substituted succinic acid.

The inventors surprisingly found out that the foregoing process for preparing a surface treated filler material product avoids the use of intensive thermal treatments and leads to a surface treated filler material product providing a sufficient hydrophilicity and very low moisture pick up susceptibility as well as a high volatile onset temperature of at least 250° C., a limited quantity of total volatiles evolved at temperatures of from 25 to 350° C., a high flash point and imparts improved mechanical properties to fibers, filaments, films and/or threads and the corresponding articles comprising said surface treated filler material product. More precisely, the inventors found out that the surface characteristics of a surface treated filler material product being obtained by said process can be improved by the addition of defined mono-substituted succinic anhydride(s).

It should be understood that for the purposes of the present invention, the following terms have the following meanings:

For the purpose of the present invention, the term "filler material" in the meaning of the present invention refers to substances of mineral origin added to materials such as paper, plastics, rubber, paints and adhesives, etc. to lower the consumption of more expensive materials such as binders, or to enhance technical properties of the products. The person skilled in the art very well knows the typical filler materials used in the respective fields. Furthermore, the term "calcium carbonate-containing filler material" refers to a material that comprises at least 80 wt.-% calcium carbonate, based on the total dry weight of the calcium carbonate-containing filler material.

The term "surface treated filler material product" in the meaning of the present invention refers to a calcium carbonate-containing filler material which has been contacted with a surface treatment agent such as to obtain a coating layer on at least a part of the surface of the calcium carbonate-containing filler material.

The term "succinic anhydride", also called dihydro-2,5-furandione, succinic acid anhydride or succinyl oxide, has the molecular formula $C_4H_4O_3$ and is the acid anhydride of succinic acid.

The term "mono-substituted" succinic anhydride in the meaning of the present invention refers to a succinic anhydride substituted with one substituent.

The term "mono-substituted" succinic acid in the meaning of the present invention refers to a succinic acid substituted with one substituent.

The term "dry" calcium carbonate-containing filler material is understood to be a filler material having less than 0.3% by weight of water relative to the filler material weight. The % water (equal to residual total moisture content) is determined according to the Coulometric Karl Fischer measurement method, wherein the filler material is heated to 220° C., and the water content released as vapour and isolated using a stream of nitrogen gas (at 100 ml/min) is determined in a Coulometric Karl Fischer unit.

The term "salty reaction products" in the meaning of the present invention refers to products obtained by contacting a calcium carbonate-containing filler material with one or more mono-substituted succinic anhydride(s). Said salty reaction products are formed between the mono-substituted succinic acid which is formed from the applied mono-substituted succinic anhydride and reactive molecules located at the surface of the calcium carbonate-containing filler material. Alternatively, said salty reaction products are formed between the mono-substituted succinic acid, which may optionally be present with the at least one mono-substituted succinic anhydride, and reactive molecules located at the surface of the calcium carbonate-containing filler material.

The term "specific surface area" (in m²/g) of the mineral filler in the meaning of the present invention is determined using the BET method with nitrogen as adsorbing gas, which is well known to the skilled man (ISO 9277:1995). The total surface area (in m²) of the mineral filler is then obtained by multiplication of the specific surface area and the mass (in g) of the mineral filler prior to treatment.

As used herein and as generally defined in the art, the "$d_{50}$" value is determined based on measurements made by using a Sedigraph™ 5100 of Micromeritics Instrument Corporation (operating instrument software version 1.04) and is defined as the size at which 50% (the median point) of the particle volume or mass is accounted for by particles having a diameter equal to the specified value. The method and the instrument are known to the skilled person and are commonly used to determine grain size of fillers and pigments. The measurement is carried out in an aqueous solution of 0.1 wt.-% $Na_4P_2O_7$. The samples are dispersed using a high speed stirrer and supersonics.

Where the term "comprising" is used in the present description and claims, it does not exclude other non-specified elements of major or minor functional importance. For the purposes of the present invention, the term "consisting of" is considered to be a preferred embodiment of the term "comprising of". If hereinafter a group is defined to comprise at least a certain number of embodiments, this is also to be understood to disclose a group, which preferably consists only of these embodiments.

Whenever the terms "including" or "having" are used, these terms are meant to be equivalent to "comprising" as defined above.

Where an indefinite or definite article is used when referring to a singular noun, e.g. "a", "an" or "the", this includes a plural of that noun unless something else is specifically stated.

According to another aspect of the present invention, a surface treated filler material product is provided, comprising a) at least one calcium carbonate-containing filler material having
   i) a weight median particle size $d_{50}$ value in the range from 0.1 to 7 µm,
   ii) a top cut $(d_{98}) \leq 15$ µm,
   iii) a specific surface area (BET) of from 0.5 to 150 m²/g as measured by the BET nitrogen method, and
   iv) a residual total moisture content of below 1 wt.-%, based on the total dry weight of the at least one calcium carbonate-containing filler material, and
b) a treatment layer on the surface of the at least one calcium carbonate-containing filler material comprising at least one mono-substituted succinic anhydride and mono-substituted succinic acid and/or salty reaction product(s) thereof, wherein the surface treated filler material product comprises the treatment layer in an amount of from 0.1 to 3 wt.-%, based on the total dry weight of the at least one calcium carbonate-containing filler material.

It is preferred that the molar ratio of the at least one mono-substituted succinic anhydride and the optional at least one mono-substituted succinic acid to the salty reaction product(s) thereof is from 0.1:99.9 to 99.9:0.1, preferably from 30:70 to 10:90. It is also preferred that the salty reaction product(s) of the at least one mono-substituted succinic anhydride and/or the at least one mono-substituted succinic acid are one or more calcium and/or magnesium salts thereof. It is further preferred that the treatment layer further comprises at least one organic material such as polysiloxanes. It is also preferred that the surface treated filler material product comprises the treatment layer in an amount of from 0.1 to 2.5 wt.-%, preferably in an amount of from 0.1 to 2 wt.-%, more preferably in an amount of from 0.1 to 1.5 wt.-%, even more preferably in an amount of from 0.1 to 1 wt.-% and most preferably in an amount of from 0.2 to 0.8 wt.-% based on the total dry weight of the at least one calcium carbonate-containing filler material.

According to a further aspect of the present invention, a polymer composition is provided, comprising at least one polymeric resin and from 1 to 85 wt.-%, based on the total weight of the polymer composition, of the surface treated filler material product. It is preferred that the at least one polymeric resin is at least one thermoplastic polymer, preferably a thermoplastic polymer selected from the group comprising homopolymers and/or copolymers of polyolefins, polyamides, halogen-containing polymers and/or polyesters. It is also preferred that the polymer composition is a masterbatch, preferably the masterbatch comprises the surface treated filler material product in an amount of from 50 to 85 wt.-%, preferably from 60 to 85 wt.-% and more preferably from 70 to 80 wt.-%, based on the total weight of the masterbatch.

According to a still further aspect of the present invention, a fiber and/or filament and/or film and/or thread is provided, comprising the surface treated filler material product and/or the polymer composition. According to another aspect of the present invention, an article comprising the surface treated filler material product and/or a polymer composition and/or a fiber and/or filament and/or film and/or thread is provided, wherein the article is selected from the group comprising hygiene products, medical and healthcare products, filter products, geotextile products, agriculture and horticulture products, clothing, footwear and baggage products, household and industrial products, packaging products, construction products and the like. According to another aspect of the present invention, the use of a mono-substituted succinic anhydride for decreasing the hydrophilicity of a calcium carbonate-containing filler material surface is provided. According to a further aspect of the present invention, the use of a surface-treated filler material product for initiating the crosslinking reaction in epoxide resins is provided.

According to one embodiment of the present invention, the at least one calcium carbonate-containing filler material of step a) is selected from among ground calcium carbonate (GCC), precipitated calcium carbonate (PCC), modified calcium carbonate (MCC) and mixtures thereof.

According to another embodiment of the present invention, the at least one calcium carbonate-containing filler material of step a) comprises at least one ground calcium carbonate (GCC) selected from the group comprising marble, chalk, dolomite, limestone and mixtures thereof and/or at least one precipitated calcium carbonate (PCC) selected from the group comprising one or more of the aragonitic, vateritic and calcitic mineralogical crystal forms and/or at least one modified calcium carbonate (MCC).

According to yet another embodiment of the present invention, the at least one calcium carbonate-containing filler material of step a) has a weight median particle size $d_{50}$ from 0.25 µm to 5 µm and preferably from 0.7 µm to 4 µm.

According to one embodiment of the present invention, the at least one calcium carbonate-containing filler material of step a) has a top cut $(d_{98})$ of $\leq 12.5$ µm, preferably of $\leq 10$ µm and most preferably of $\leq 7.5$ µm.

According to another embodiment of the present invention, the at least one calcium carbonate-containing filler material of step a) has a specific surface area (BET) of from 0.5 to 50 m²/g, more preferably of from 0.5 to 35 m²/g and most preferably of from 0.5 to 15 m²/g as measured by the BET nitrogen method.

According to yet another embodiment of the present invention, the at least one calcium carbonate-containing filler material of step a) has a residual total moisture content of from 0.01 to 0.2 wt.-%, preferably from 0.02 to 0.15 wt.-% and most preferably from 0.04 to 0.15 wt.-%, based on the total dry weight of the at least one calcium carbonate-containing filler material.

According to one embodiment of the present invention, the at least one calcium carbonate-containing filler material of step a) is preheated before contacting step c) is carried out, preferably the at least one calcium carbonate-containing filler material of step a) is preheated at a temperature of from 50 to 200° C., more preferably of from 80 to 200° C., even more preferably of from 90 to 150° C. and most preferably of from 100 to 130° C.

According to another embodiment of the present invention, the at least one mono-substituted succinic anhydride and the optional at least one mono-substituted succinic acid of step b) are provided in a total amount of from 0.1 to 2.5 wt.-%, preferably in an amount of from 0.1 to 2 wt.-%, more preferably in an amount of from 0.1 to 1.5 wt.-%, even more preferably in an amount of from 0.1 to 1 wt.-% and most preferably in an amount of from 0.2 to 0.8 wt.-% based on the total dry weight of the at least one calcium carbonate-containing filler material.

According to yet another embodiment of the present invention, the at least one mono-substituted succinic anhydride of step b) consists of succinic anhydride mono-substituted with a group selected from a linear, branched, aliphatic and cyclic group having a total amount of carbon atoms from C2 to C30, preferably from C3 to C25 and most preferably from C4 to C20 in the substituent.

According to one embodiment of the present invention, the at least one mono-substituted succinic anhydride of step b) is at least one alkyl mono-substituted succinic anhydride, preferably at least one alkyl mono-substituted succinic anhydride selected from the group comprising ethylsuccinic anhydride, propylsuccinic anhydride, butylsuccinic anhydride, triisobutyl succinic anhydride, pentylsuccinic anhydride, hexylsuccinic anhydride, heptylsuccinic anhydride, octylsuccinic anhydride, nonylsuccinic anhydride, decyl succinic anhydride, dodecyl succinic anhydride, hexadecanyl succinic anhydride, octadecanyl succinic anhydride, and mixtures thereof.

According to another embodiment of the present invention, the at least one mono-substituted succinic anhydride of step b) is at least one alkenyl mono-substituted succinic anhydride, preferably at least one alkenyl mono-substituted succinic anhydride selected from the group comprising ethenylsuccinic anhydride, propenylsuccinic anhydride, butenylsuccinic anhydride, triisobutenyl succinic anhydride, pentenylsuccinic anhydride, hexenylsuccinic anhydride, heptenylsuccinic anhydride, octenylsuccinic anhydride, nonenylsuccinic anhydride, decenyl succinic anhydride, dodecenyl succinic anhydride, hexadecenyl succinic anhydride, octadecenyl succinic anhydride, and mixtures thereof.

According to yet another embodiment of the present invention, the at least one mono-substituted succinic anhydride and the optional at least one mono-substituted succinic acid of step b) are added in contacting step c) in a total amount of from 0.1 to 2 wt.-%, preferably of from 0.2 to 1.5 wt.-% and most preferably of from 0.3 to 1 wt.-%, based on the total dry weight of the at least one calcium carbonate-containing filler material of step a).

According to one embodiment of the present invention, the at least one mono-substituted succinic acid of step b) is present in an amount of ≤10 mol.-%, based on the molar sum of the at least one mono-substituted succinic anhydride and the at least one mono-substituted succinic acid.

According to another embodiment of the present invention, contacting step c) is carried out at a temperature of from 30 to 200° C., preferably of from 80 to 150° C. and most preferably of from 110 to 130° C.

According to yet another embodiment of the present invention, contacting step c) is carried out in a batch or continuous process, preferably for a period of time from 0.1 to 1000 seconds. It is preferred that contacting step c) is a continuous process and comprises one or several contacting steps and the total contacting time is from 0.1 to 20 s, preferably from 0.5 to 15 s and most preferably from 1 to 10 s.

According to one embodiment of the present invention, the salty reaction product(s) of the mono-substituted succinic acid and/or the at least one mono-substituted succinic acid formed on the surface of said at least one calcium carbonate-containing filler material in step c) are one or more calcium salts and/or magnesium salts thereof.

According to another embodiment of the present invention, the process further comprises step d) of contacting the at least one calcium carbonate-containing filler material of step a), in one or more steps, with at least one organic material such as polysiloxanes. It is preferred that contacting step d) is carried out during and/or after contacting step c), preferably after contacting step c). It is further preferred that contacting step d) is carried out at a temperature of from 40 to 200° C., preferably of from 50 to 150° C. and most preferably of from 60 to 120° C. It is also preferred that at least one organic material is added in contacting step d) in an amount of from 100 to 1 000 ppm, preferably from 200 to 800 ppm and most preferably from 300 to 700 ppm, based on the total dry weight of the at least one calcium carbonate-containing filler material of step a).

According to yet another embodiment of the present invention, the obtained surface treated filler material product has a water pick-up of from 0.1 to 0.8 mg/g, preferably of from 0.2 to 0.7 mg/g and most preferably of from 0.2 to 0.6 mg/g at a temperature of 23° C. (±2° C.).

According to one embodiment of the present invention, the obtained surface treated filler material product has a volatile onset temperature of ≥250° C., preferably of ≥260° C. and most preferably of ≥270° C.

According to another embodiment of the present invention, the obtained surface treated filler material product has a hydrophilicity of below 8:2 volumetric ratio of water:ethanol measured at +23° C. (±2° C.) with the sedimentation method.

As set out above, the inventive process for preparing a surface treated filler material product with succinic anhydrides comprises at least the process steps of a), b) and c). In the following, it is referred to further details of the present invention and especially the foregoing steps of the inventive process for preparing a surface treated filler material product.

Characterization of Step a): Provision of at Least One Calcium Carbonate-Containing Filler Material According to step a) of the process of the present invention, at least one calcium carbonate-containing filler material is provided.

The at least one calcium carbonate-containing filler material in the meaning of the present invention refers to a filler material selected from among ground (or natural) calcium carbonate (GCC), a precipitated calcium carbonate (PCC), a modified calcium carbonate (MCC) and mixtures thereof.

GCC is understood to be a naturally occurring form of calcium carbonate, mined from sedimentary rocks such as limestone or chalk, or from metamorphic marble rocks and processed through a treatment such as grinding, screening and/or fractionizing in wet and/or dry form, for example by a cyclone or classifier. In one embodiment of the present invention, the GCC is selected from the group comprising marble, chalk, dolomite, limestone and mixtures thereof.

By contrast, calcium carbonate of the PCC type include synthetic calcium carbonate products obtained by carbonation of a slurry of calcium hydroxide, commonly referred to in the art as a slurry of lime or milk of lime when derived from finely divided calcium oxide particles in water or by precipitation out of an ionic salt solution. PCC may be rhombohedral and/or scalenohedral and/or aragonitic; preferred synthetic calcium carbonate or precipitated calcium carbonate comprising aragonitic, vateritic or calcitic mineralogical crystal forms or mixtures thereof.

"Modified calcium carbonate" in the meaning of the present invention may feature a natural ground or precipitated calcium carbonate with an internal structure modification or a surface-reaction product. According to a preferred embodiment of the present invention, the modified calcium carbonate is a surface-reacted calcium carbonate.

In one preferred embodiment, the at least one calcium carbonate-containing filler material is marble.

It is appreciated that the amount of calcium carbonate in the at least one calcium carbonate-containing filler material is at least 80 wt.-%, e.g. at least 95 wt.-%, preferably between 97 and 100 wt.-%, more preferably between 98.5 and 99.95 wt.-%, based on the total dry weight of the at least one calcium carbonate-containing filler material.

The at least one calcium carbonate-containing filler material is preferably in the form of a particulate material, and may have a particle size distribution as conventionally employed for the material(s) involved in the type of product to be produced. In general, it is one specific requirement of the present invention that the at least one calcium carbonate-containing filler material has a weight median particle size $d_{50}$ value in the range from 0.1 to 7 µm. For example, the at least one calcium carbonate-containing filler material has a weight median particle size $d_{50}$ from 0.25 µm to 5 µm and preferably from 0.7 µm to 4 µm.

A further requirement of the present invention is that the at least one calcium carbonate-containing filler material has a top cut ($d_{98}$) of ≤15 µm. For example, the at least one calcium carbonate-containing filler material has a top cut ($d_{98}$) of ≤12.5 µm, preferably of ≤10 µm and most preferably of ≤7.5 µm.

It is further appreciated that the at least one calcium carbonate-containing filler material has a BET specific surface area of from 0.5 and 150 m²/g as measured by the BET nitrogen method according to ISO 9277. For example, the at least one calcium carbonate-containing filler material has a specific surface area (BET) of from 0.5 to 50 m²/g, more preferably of from 0.5 to 35 m²/g and most preferably of from 0.5 to 15 m²/g as measured by the BET nitrogen method according to ISO 9277.

In one embodiment of the present invention, the at least one calcium carbonate-containing filler material is preferably a marble having a median particle size diameter $d_{50}$ value from 0.1 µm to 7 µm, preferably from 0.25 µm to 5 µm and most preferably from 0.7 µm to 4 µm. In this case, the at least one calcium carbonate-containing filler material exhibits a BET specific surface area of from 0.5 to 150 m²/g, preferably of from 0.5 to 50 m²/g, more preferably of from 0.5 to 35 m²/g and most preferably of from 0.5 to 15 m²/g, measured using nitrogen and the BET method according to ISO 9277.

It is preferred that the at least one calcium carbonate-containing filler material is a dry ground material, a material being wet ground and dried or a mixture of the foregoing materials. In general, the grinding step can be carried out with any conventional grinding device, for example, under conditions such that refinement predominantly results from impacts with a secondary body, i.e. in one or more of: a ball mill, a rod mill, a vibrating mill, a roll crusher, a centrifugal impact mill, a vertical bead mill an attrition mill, a pin mill, a hammer mill, a pulveriser, a shredder, a de-clumper, a knife cutter, or other such equipment known to the skilled man.

In case the at least one calcium carbonate-containing filler material is a wet ground calcium carbonate-containing filler material, the grinding step may be performed under conditions such that autogenous grinding takes place and/or by horizontal ball milling, and/or other such processes known to the skilled man. The wet processed ground calcium carbonate-containing filler material thus obtained may be washed and dewatered by well known processes, e.g. by flocculation, filtration or forced evaporation prior to drying. The subsequent step of drying may be carried out in a single step such as spray drying, or in at least two steps, e.g. by applying a first heating step to the calcium carbonate-containing filler material in order to reduce the associated moisture content to a level which is not greater than about 0.5 wt.-%, based on the total dry weight of the at least one calcium carbonate-containing filler material. The residual total moisture content of the filler can be measured by the Karl Fischer coulometric titration method, desorbing the moisture in an oven at 195° C. and passing it continuously into the KF coulometer (Mettler Toledo coulometric KF Titrator C30, combined with Mettler oven DO 0337) using dry $N_2$ at 100 ml/min for 10 min. The residual total moisture content can be determined with a calibration curve and also a blind of 10 min gas flow without a sample can be taken into account. The residual total moisture content may be further reduced by applying a second heating step to the at least one calcium carbonate-containing filler material. In case said drying is carried out by more than one drying steps, the first step may be carried out by heating in a hot current of air, while the second and further drying steps are preferably carried out by an indirect heating in which the atmosphere in the corresponding vessel comprises a surface treatment agent. It is also common that the at least one calcium carbonate-containing filler material is subjected to a beneficiation step (such as a flotation, bleaching or magnetic separation step) to remove impurities.

In one embodiment of the present invention, the at least one calcium carbonate-containing filler material comprises a dry ground calcium carbonate-containing filler material. In another preferred embodiment, the at least one calcium carbonate-containing filler material is a material being wet ground in a horizontal ball mill, and subsequently dried by using the well known process of spray drying.

Depending on the at least one calcium carbonate-containing filler material, the at least one calcium carbonate-containing filler material has a residual total moisture content of from 0.01 to 1 wt.-%, preferably from 0.01 to 0.2 wt.-%, more preferably from 0.02 to 0.15 wt.-% and most preferably from 0.04 to 0.15 wt.-%, based on the total dry weight of the at least one calcium carbonate-containing filler material.

For example, in case a wet ground and spray dried marble is used as the at least one calcium carbonate-containing filler material, the residual total moisture content of the at least one calcium carbonate-containing filler material is preferably of from 0.01 to 0.1 wt.-%, more preferably from 0.02 to 0.08 wt.-% and most preferably from 0.04 to 0.07 wt.-% based on the total dry weight of the at least one calcium carbonate-containing filler material. If a PCC is used as the at least one calcium carbonate-containing filler material, the residual total moisture content of the at least one calcium carbonate-containing filler material is preferably of from 0.01 to 0.2 wt.-%, more preferably from 0.05 to 0.17 wt.-% and most preferably from 0.05 to 0.10 wt.-%, based on the total dry weight of the at least one calcium carbonate-containing filler material.

Characterization of Step b): Provision of at Least One Mono-Substituted Succinic Anhydride According to step b) of the process of the present invention at least one mono-substituted succinic anhydride and optionally at least one mono-substituted succinic acid are provided.

It is appreciated that the expression "at least one" mono-substituted succinic anhydride means that one or more kinds of mono-substituted succinic anhydride may be provided in the process of the present invention.

Accordingly, it should be noted that the at least one mono-substituted succinic anhydride may be one kind of mono-substituted succinic anhydride. Alternatively, the at least one mono-substituted succinic anhydride may be a mixture of two or more kinds of mono-substituted succinic anhydride. For example, the at least one mono-substituted succinic anhydride may be a mixture of two or three kinds of mono-substituted succinic anhydride, like two kinds of mono-substituted succinic anhydride.

In one embodiment of the present invention, the at least one mono-substituted succinic anhydride is one kind of mono-substituted succinic anhydride.

It is appreciated that the at least one mono-substituted succinic anhydride represents a surface treatment agent and consists of succinic anhydride mono-substituted with a group selected from any linear, branched, aliphatic and cyclic group having a total amount of carbon atoms from C2 to C30 in the substituent.

In one embodiment of the present invention, the at least one mono-substituted succinic anhydride consists of succinic anhydride mono-substituted with a group selected from a linear, branched, aliphatic and cyclic group having a total amount of carbon atoms from C3 to C20 in the substituent. For example, the at least one mono-substituted succinic anhydride consists of succinic anhydride mono-substituted with a group selected from a linear, branched, aliphatic and cyclic group having a total amount of carbon atoms from C4 to C18 in the substituent.

In one embodiment of the present invention, the at least one mono-substituted succinic anhydride consists of succinic anhydride mono-substituted with one group being a linear and aliphatic group having a total amount of carbon atoms from C2 to C30, preferably from C3 to C20 and most preferably from C4 to C18 in the substituent. Additionally or alternatively, the at least one mono-substituted succinic anhydride consists of succinic anhydride mono-substituted with one group being a branched and aliphatic group having a total amount of carbon atoms from C2 to C30, preferably from C3 to C20 and most preferably from C4 to C18 in the substituent.

Thus, it is preferred that the at least one mono-substituted succinic anhydride consists of succinic anhydride mono-substituted with one group being a linear or branched, alkyl group having a total amount of carbon atoms from C2 to C30, preferably from C3 to C20 and most preferably from C4 to C18 in the substituent.

For example, the at least one mono-substituted succinic anhydride consists of succinic anhydride mono-substituted with one group being a linear alkyl group having a total amount of carbon atoms from C2 to C30, preferably from C3 to C20 and most preferably from C4 to C18 in the substituent. Additionally or alternatively, the at least one mono-substituted succinic anhydride consists of succinic anhydride mono-substituted with one group being a branched alkyl group having a total amount of carbon atoms from C2 to C30, preferably from C3 to C20 and most preferably from C4 to C18 in the substituent.

The term "alkyl" in the meaning of the present invention refers to a linear or branched, saturated organic compound composed of carbon and hydrogen. In other words, "alkyl mono-substituted succinic anhydrides" are composed of linear or branched, saturated hydrocarbon chains containing a pendant succinic anhydride group.

In one embodiment of the present invention, the at least one mono-substituted succinic anhydride is at least one linear or branched alkyl mono-substituted succinic anhydride. For example, the at least one alkyl mono-substituted succinic anhydride is selected from the group comprising ethylsuccinic anhydride, propylsuccinic anhydride, butylsuccinic anhydride, triisobutyl succinic anhydride, pentylsuccinic anhydride, hexylsuccinic anhydride, heptylsuccinic anhydride, octylsuccinic anhydride, nonylsuccinic anhydride, decyl succinic anhydride, dodecyl succinic anhydride, hexadecanyl succinic anhydride, octadecanyl succinic anhydride, and mixtures thereof.

Accordingly, it is appreciated that e.g. the term "butylsuccinic anhydride" comprises linear and branched butylsuccinic anhydride(s). One specific example of linear butylsuccinic anhydride(s) is n-butylsuccinic anhydride. Specific examples of branched butylsuccinic anhydride(s) are iso-butylsuccinic anhydride, sec-butylsuccinic anhydride and/or tert-butylsuccinic anhydride.

Furthermore, it is appreciated that e.g. the term "hexadecanyl succinic anhydride" comprises linear and branched hexadecanyl succinic anhydride(s). One specific example of linear hexadecanyl succinic anhydride(s) is n-hexadecanyl succinic anhydride. Specific examples of branched hexadecanyl succinic anhydride(s) are 14-methylpentadecanyl succinic anhydride, 13-methylpentadecanyl succinic anhydride, 12-methylpentadecanyl succinic anhydride, 11-methylpentadecanyl succinic anhydride, 10-methylpentadecanyl succinic anhydride, 9-methylpentadecanyl succinic anhydride, 8-methylpentadecanyl succinic anhydride, 7-methylpentadecanyl succinic anhydride, 6-methylpentadecanyl succinic anhydride, 5-methylpentadecanyl succinic anhydride, 4-methylpentadecanyl succinic anhydride, 3-methylpentadecanyl succinic anhydride, 2-methylpentadecanyl succinic anhydride, 1-methylpentadecanyl succinic anhydride, 13-ethylbutadecanyl succinic anhydride, 12-ethylbutadecanyl succinic anhydride, 11-ethylbutadecanyl succinic anhydride, 10-ethylbutadecanyl succinic anhydride, 9-ethylbutadecanyl succinic anhydride, 8-ethylbutadecanyl succinic anhydride, 7-ethylbutadecanyl succinic anhydride, 6-ethylbutadecanyl succinic anhydride, 5-ethylbutadecanyl succinic anhydride, 4-ethylbutadecanyl succinic anhydride, 3-ethylbutadecanyl succinic anhydride, 2-ethylbutadecanyl succinic anhydride, 1-ethylbutadecanyl succinic anhydride, 2-butyldodecanyl succinic anhydride, 1-hexyldecanyl succinic anhydride, 1-hexyl-2-decanyl succinic anhydride, 2-hexyldecanyl succinic anhydride, 6,12-dimethylbutadecanyl succinic anhydride, 2,2-diethyldodecanyl succinic anhydride, 4,8,12-trimethyltridecanyl succinic anhydride, 2,2,4,6,8-pentamethylundecanyl succinic anhydride, 2-ethyl-4-methyl-2-(2-methylpentyl)-heptyl succinic anhydride and/or 2-ethyl-4,6-dimethyl-2-propylnonyl succinic anhydride.

Furthermore, it is appreciated that e.g. the term "octadecanyl succinic anhydride" comprises linear and branched octadecanyl succinic anhydride(s). One specific example of linear octadecanyl succinic anhydride(s) is n-octadecanyl succinic anhydride. Specific examples of branched hexadecanyl succinic anhydride(s) are 16-methylheptadecanyl succinic anhydride, 15-methylheptadecanyl succinic anhydride, 14-methylheptadecanyl succinic anhydride, 13-methylheptadecanyl succinic anhydride, 12-methylheptadecanyl succinic anhydride, 11-methylheptadecanyl succinic anhydride, 10-methylheptadecanyl succinic anhydride, 9-methylheptadecanyl succinic anhydride, 8-methylheptadecanyl succinic anhydride, 7-methylheptadecanyl succinic anhydride, 6-methylheptadecanyl succinic anhydride, 5-methylheptadecanyl succinic anhydride, 4-methylheptadecanyl succinic anhydride, 3-methylheptadecanyl succinic anhydride, 2-methylheptadecanyl succinic anhydride, 1-methylheptadecanyl succinic anhydride, 14-ethylhexadecanyl succinic anhydride, 13-ethylhexadecanyl succinic anhydride, 12-ethylhexadecanyl succinic anhydride, 11-ethylhexadecanyl succinic anhydride, 10-ethylhexadecanyl succinic anhydride, 9-ethylhexadecanyl succinic anhydride, 8-ethylhexadecanyl succinic anhydride, 7-ethylhexadecanyl succinic anhydride, 6-ethylhexadecanyl succinic anhydride, 5-ethylhexadecanyl succinic anhydride, 4-ethylhexadecanyl succinic anhydride, 3-ethylhexadecanyl succinic anhydride, 2-ethylhexadecanyl succinic anhydride, 1-ethylhexadecanyl succinic anhydride, 2-hexyldodecanyl succinic anhydride, 2-heptylundecanyl succinic anhydride, iso-octadecanyl succinic anhydride and/or 1-octyl-2-decanyl succinic anhydride.

In one embodiment of the present invention, the at least one alkyl mono-substituted succinic anhydride is selected from the group comprising butylsuccinic anhydride, hexylsuccinic anhydride, heptylsuccinic anhydride, octylsuccinic anhydride, hexadecanyl succinic anhydride, octadecanyl succinic anhydride, and mixtures thereof.

In one embodiment of the present invention, the at least one mono-substituted succinic anhydride is one kind of alkyl mono-substituted succinic anhydride. For example, the one alkyl mono-substituted succinic anhydride is butylsuccinic anhydride. Alternatively, the one alkyl mono-substituted succinic anhydride is hexylsuccinic anhydride. Alternatively, the one alkyl mono-substituted succinic anhydride is heptylsuccinic anhydride or octylsuccinic anhydride. Alternatively, the one alkyl mono-substituted succinic anhydride is hexadecanyl succinic anhydride. For example, the one alkyl mono-substituted succinic anhydride is linear hexadecanyl succinic anhydride such as n-hexadecanyl succinic anhydride or branched hexadecanyl succinic anhydride such as 1-hexyl-2-decanyl succinic anhydride. Alternatively, the one alkyl mono-substituted succinic anhydride is octadecanyl succinic anhydride. For example, the one alkyl mono-substituted succinic anhydride is linear octadecanyl succinic anhydride such as n-octadecanyl succinic anhydride or branched octadecanyl succinic anhydride such as iso-octadecanyl succinic anhydride or 1-octyl-2-decanyl succinic anhydride.

In one embodiment of the present invention, the one alkyl mono-substituted succinic anhydride is butylsuccinic anhydride such as n-butylsuccinic anhydride.

In one embodiment of the present invention, the at least one mono-substituted succinic anhydride is a mixture of two or more kinds of alkyl mono-substituted succinic anhydrides. For example, the at least one mono-substituted succinic anhydride is a mixture of two or three kinds of alkyl mono-substituted succinic anhydrides.

In one embodiment of the present invention, the at least one mono-substituted succinic anhydride consists of succinic anhydride mono-substituted with one group being a linear or branched alkenyl group having a total amount of carbon atoms from C2 to C30, preferably from C3 to C20 and most preferably from C4 to C18 in the substituent.

The term "alkenyl" in the meaning of the present invention refers to a linear or branched, unsaturated organic compound composed of carbon and hydrogen. Said organic compound further contains at least one double bond in the substituent, preferably one double bond. In other words, "alkenyl mono-substituted succinic anhydrides" are composed of linear or branched, unsaturated hydrocarbon chains containing a pendant succinic anhydride group. It is appreciated that the term "alkenyl" in the meaning of the present invention includes the cis and trans isomers.

In one embodiment of the present invention, the at least one mono-substituted succinic anhydride is at least one linear or branched alkenyl mono-substituted succinic anhydride. For example, the at least one alkenyl mono-substituted succinic anhydride is selected from the group comprising ethenylsuccinic anhydride, propenylsuccinic anhydride, butenylsuccinic anhydride, triisobutenyl succinic anhydride, pentenylsuccinic anhydride, hexenylsuccinic anhydride, heptenylsuccinic anhydride, octenylsuccinic anhydride, nonenylsuccinic anhydride, decenyl succinic anhydride, dodecenyl succinic anhydride, hexadecenyl succinic anhydride, octadecenyl succinic anhydride, and mixtures thereof.

Accordingly, it is appreciated that e.g. the term "hexadecenyl succinic anhydride" comprises linear and branched hexadecenyl succinic anhydride(s). One specific example of linear hexadecenyl succinic anhydride(s) is n-hexadecenyl succinic anhydride such as 14-hexadecenyl succinic anhydride, 13-hexadecenyl succinic anhydride, 12-hexadecenyl succinic anhydride, 11-hexadecenyl succinic anhydride, 10-hexadecenyl succinic anhydride, 9-hexadecenyl succinic anhydride, 8-hexadecenyl succinic anhydride, 7-hexadecenyl succinic anhydride, 6-hexadecenyl succinic anhydride, 5-hexadecenyl succinic anhydride, 4-hexadecenyl succinic anhydride, 3-hexadecenyl succinic anhydride and/or 2-hexadecenyl succinic anhydride. Specific examples of branched hexadecenyl succinic anhydride(s) are 14-methyl-9-pentadecenyl succinic anhydride, 14-methyl-2-pentadecenyl succinic anhydride, 1-hexyl-2-decenyl succinic anhydride and/or iso-hexadecenyl succinic anhydride.

Furthermore, it is appreciated that e.g. the term "octadecenyl succinic anhydride" comprises linear and branched octadecenyl succinic anhydride(s). One specific example of linear octadecenyl succinic anhydride(s) is n-octadecenyl succinic anhydride such as 16-octadecenyl succinic anhydride, 15-octadecenyl succinic anhydride, 14-octadecenyl succinic anhydride, 13-octadecenyl succinic anhydride, 12-octadecenyl succinic anhydride, 11-octadecenyl succinic anhydride, 10-octadecenyl succinic anhydride, 9-octadecenyl succinic anhydride, 8-octadecenyl succinic anhydride, 7-octadecenyl succinic anhydride, 6-octadecenyl succinic anhydride, 5-octadecenyl succinic anhydride, 4-octadecenyl succinic anhydride, 3-octadecenyl succinic anhydride and/or 2-octadecenyl succinic anhydride. Specific examples of branched octadecenyl succinic anhydride(s) are 16-methyl-9-heptadecenyl succinic anhydride, 16-methyl-7-heptadecenyl succinic anhydride, 1-octyl-2-decenyl succinic anhydride and/or iso-octadecenyl succinic anhydride.

In one embodiment of the present invention, the at least one alkenyl mono-substituted succinic anhydride is selected from the group comprising hexenylsuccinic anhydride, octenylsuccinic anhydride, hexadecenyl succinic anhydride, octadecenyl succinic anhydride, and mixtures thereof.

In one embodiment of the present invention, the at least one mono-substituted succinic anhydride is one alkenyl mono-substituted succinic anhydride. For example, the one alkenyl mono-substituted succinic anhydride is hexenylsuccinic anhydride. Alternatively, the one alkenyl mono-substituted succinic anhydride is octenylsuccinic anhydride. Alternatively, the one alkenyl mono-substituted succinic anhydride is hexadecenyl succinic anhydride. For example, the one alkenyl mono-substituted succinic anhydride is linear hexadecenyl succinic anhydride such as n-hexadecenyl succinic anhydride or branched hexadecenyl succinic anhydride such as 1-hexyl-2-decenyl succinic anhydride. Alternatively, the one alkenyl mono-substituted succinic anhydride is octadecenyl succinic anhydride. For example, the one alkyl mono-substituted succinic anhydride is linear octadecenyl succinic anhydride such as n-octadecenyl succinic anhydride or branched octadecenyl succinic anhydride such iso-octadecenyl succinic anhydride, or 1-octyl-2-decenyl succinic anhydride.

In one embodiment of the present invention, the one alkenyl mono-substituted succinic anhydride is linear octadecenyl succinic anhydride such as n-octadecenyl succinic anhydride. In another embodiment of the present invention, the one alkenyl mono-substituted succinic anhydride is linear octenylsuccinic anhydride such as n-octenylsuccinic anhydride.

If the at least one mono-substituted succinic anhydride is one alkenyl mono-substituted succinic anhydride, it is appreciated that the one alkenyl mono-substituted succinic anhydride is present in an amount of ≥95 wt.-% and preferably of ≥96.5 wt.-%, based on the total weight of the at least one mono-substituted succinic anhydride provided in step b).

In one embodiment of the present invention, the at least one mono-substituted succinic anhydride is a mixture of two or more kinds of alkenyl mono-substituted succinic anhydrides. For example, the at least one mono-substituted succinic anhydride is a mixture of two or three kinds of alkenyl mono-substituted succinic anhydrides.

If the at least one mono-substituted succinic anhydride is a mixture of two or more kinds of alkenyl mono-substituted succinic anhydrides, one alkenyl mono-substituted succinic anhydride is linear or branched octadecenyl succinic anhydride, while each further alkenyl mono-substituted succinic anhydride is selected from ethenylsuccinic anhydride, propenylsuccinic anhydride, butenylsuccinic anhydride, pentenylsuccinic anhydride, hexenylsuccinic anhydride, heptenylsuccinic anhydride, nonenylsuccinic anhydride, hexadecenyl succinic anhydride and mixtures thereof. For example, the at least one mono-substituted succinic anhydride is a mixture of two or more kinds of alkenyl mono-substituted succinic anhydrides, wherein one alkenyl mono-substituted succinic anhydride is linear octadecenyl succinic anhydride and each further alkenyl mono-substituted succinic anhydride is selected from ethenylsuccinic anhydride, propenylsuccinic anhydride, butenylsuccinic anhydride, pentenylsuccinic anhydride, hexenylsuccinic anhydride, heptenylsuccinic anhydride, nonenylsuccinic anhydride, hexadecenyl succinic anhydride and mixtures thereof. Alternatively, the at least one mono-substituted succinic anhydride is a mixture of two or more kinds of alkenyl mono-substituted succinic anhydrides, wherein one alkenyl mono-substituted succinic anhydride is branched octadecenyl succinic anhydride and each further alkenyl mono-substituted succinic anhydride is selected from ethenylsuccinic anhydride, propenylsuccinic anhydride, butenylsuccinic anhydride, pentenylsuccinic anhydride, hexenylsuccinic anhydride, heptenylsuccinic anhydride, nonenylsuccinic anhydride, hexadecenyl succinic anhydride and mixtures thereof.

For example, the at least one mono-substituted succinic anhydride is a mixture of two or more kinds of alkenyl mono-substituted succinic anhydrides comprising one or more hexadecenyl succinic anhydride, like linear or branched hexadecenyl succinic anhydride(s), and one or more octadecenyl succinic anhydride, like linear or branched octadecenyl succinic anhydride(s).

In one embodiment of the present invention, the at least one mono-substituted succinic anhydride is a mixture of two or more kinds of alkenyl mono-substituted succinic anhydrides comprising linear hexadecenyl succinic anhydride(s) and linear octadecenyl succinic anhydride(s). Alternatively, the at least one mono-substituted succinic anhydride is a mixture of two or more kinds of alkenyl mono-substituted succinic anhydrides comprising branched hexadecenyl succinic anhydride(s) and branched octadecenyl succinic anhydride(s). For example, the one or more hexadecenyl succinic anhydride is linear hexadecenyl succinic anhydride like n-hexadecenyl succinic anhydride and/or branched hexadecenyl succinic anhydride like 1-hexyl-2-decenyl succinic anhydride. Additionally or alternatively, the one or more octadecenyl succinic anhydride is linear octadecenyl succinic anhydride like n-octadecenyl succinic anhydride and/or branched octadecenyl succinic anhydride like iso-octadecenyl succinic anhydride and/or 1-octyl-2-decenyl succinic anhydride.

If the at least one mono-substituted succinic anhydride is a mixture of two or more kinds of alkenyl mono-substituted succinic anhydrides, it is appreciated that one alkenyl mono-substituted succinic anhydride is present in an amount of from 20 to 60 wt.-% and preferably of from 30 to 50 wt.-%, based on the total weight of the at least one mono-substituted succinic anhydride provided in step b).

For example, if the at least one mono-substituted succinic anhydride is a mixture of two or more kinds of alkenyl mono-substituted succinic anhydrides comprising one or more hexadecenyl succinic anhydride(s), like linear or branched hexadecenyl succinic anhydride(s), and one or more octadecenyl succinic anhydride(s), like linear or branched hexadecenyl succinic anhydride(s), it is preferred that the one or more octadecenyl succinic anhydride(s) is present in an amount of from 20 to 60 wt.-% and preferably of from 30 to 50 wt.-%, based on the total weight of the at least one mono-substituted succinic anhydride provided in step b).

It is also appreciated that the at least one mono-substituted succinic anhydride may be a mixture of at least one alkyl mono-substituted succinic anhydrides and at least one alkenyl mono-substituted succinic anhydrides.

If the at least one mono-substituted succinic anhydride is a mixture of at least one alkyl mono-substituted succinic anhydrides and at least one alkenyl mono-substituted succinic anhydrides, it is appreciated that the alkyl substituent of the of at least one alkyl mono-substituted succinic anhydrides and the alkenyl substituent of the of at least one alkenyl mono-substituted succinic anhydrides are preferably the same. For example, the at least one mono-substituted succinic anhydride is a mixture of ethylsuccinic anhydride and ethenylsuccinic anhydride. Alternatively, the at least one mono-substituted succinic anhydride is a mixture of propylsuccinic anhydride and propenylsuccinic anhydride. Alternatively, the at least one mono-substituted succinic anhydride is a mixture of butylsuccinic anhydride and butenylsuccinic anhydride. Alternatively, the at least one mono-substituted succinic anhydride is a mixture of tri-isobutyl succinic anhydride and triisobutenyl succinic anhydride. Alternatively, the at least one mono-substituted succinic anhydride is a mixture of pentylsuccinic anhydride and pentenylsuccinic anhydride. Alternatively, the at least one mono-substituted succinic anhydride is a mixture of hexylsuccinic anhydride and hexenylsuccinic anhydride. Alternatively, the at least one mono-substituted succinic anhydride is a mixture of heptylsuccinic anhydride and heptenylsuccinic anhydride. Alternatively, the at least one mono-substituted succinic anhydride is a mixture of octylsuccinic anhydride and octenylsuccinic anhydride. Alternatively, the at least one mono-substituted succinic anhydride is a mixture of nonylsuccinic anhydride and nonenylsuccinic anhydride. Alternatively, the at least one mono-substituted succinic anhydride is a mixture of decyl succinic anhydride and decenyl succinic anhydride. Alternatively, the at least one mono-substituted succinic anhydride is a mixture of dodecyl succinic anhydride and dodecenyl succinic anhydride. Alternatively, the at least one mono-substituted succinic anhydride is a mixture of hexadecanyl succinic anhydride and hexadecenyl succinic anhydride. For example, the at least one mono-substituted succinic anhydride is a mixture of linear hexadecanyl succinic anhydride and linear hexadecenyl succinic anhydride or a mixture of branched hexadecanyl succinic anhydride and branched hexadecenyl succinic anhydride. Alternatively, the at least one mono-substituted succinic anhydride is a mixture of octadecanyl succinic anhydride and octadecenyl succinic anhydride. For example, the at least one mono-substituted succinic anhydride is a mixture of linear octadecanyl succinic anhydride and linear octadecenyl succinic anhydride or a mixture of branched octadecanyl succinic anhydride and branched octadecenyl succinic anhydride.

In one embodiment of the present invention, the at least one mono-substituted succinic anhydride is a mixture of nonylsuccinic anhydride and nonenylsuccinic anhydride.

If the at least one mono-substituted succinic anhydride is a mixture of at least one alkyl mono-substituted succinic anhydrides and at least one alkenyl mono-substituted succinic anhydrides, the weight ratio between the at least one alkyl mono-substituted succinic anhydride and the at least one alkenyl mono-substituted succinic anhydride is between 90:10 and 10:90 (wt.-%/wt.-%). For example, the weight ratio between the at least one alkyl mono-substituted succinic anhydride and the at least one alkenyl mono-substituted succinic anhydride is between 70:30 and 30:70 (wt.-%/wt.-%) or between 60:40 and 40:60.

Optionally, at least one mono-substituted succinic acid is provided according to step b) of the inventive process.

It is appreciated that the expression "at least one" mono-substituted succinic acid means that one or more kinds of mono-substituted succinic acid may be provided in the process of the present invention.

Accordingly, it should be noted that the at least one mono-substituted succinic acid may be one kind of mono-substituted succinic acid. Alternatively, the at least one mono-substituted succinic acid may be a mixture of two or more kinds of mono-substituted succinic acid. For example, the at least one mono-substituted succinic acid may be a mixture of two or three kinds of mono-substituted succinic acid, like two kinds of mono-substituted succinic acid.

In one embodiment of the present invention, the at least one mono-substituted succinic acid is one kind of mono-substituted succinic acid.

It is appreciated that the at least one mono-substituted succinic acid represents a surface treatment agent and consists of succinic acid mono-substituted with a group selected from any linear, branched, aliphatic and cyclic group having a total amount of carbon atoms from C2 to C30 in the substituent.

In one embodiment of the present invention, the at least one mono-substituted succinic acid consists of succinic acid mono-substituted with a group selected from a linear, branched, aliphatic and cyclic group having a total amount of carbon atoms from C3 to C20 in the substituent. For example, the at least one mono-substituted succinic acid consists of succinic acid mono-substituted with a group selected from a linear, branched, aliphatic and cyclic group having a total amount of carbon atoms from C4 to C18 in the substituent.

It is appreciated that the at least one mono-substituted succinic anhydride and the at least one mono-substituted succinic acid may comprise the same or different substituent.

In one embodiment of the present invention, the succinic acid molecule of the at least one mono-substituted succinic acid and the succinic anhydride molecule of the at least one mono-substituted succinic anhydride are mono-substituted with the same group selected from any linear, branched, aliphatic and cyclic group having a total amount of carbon atoms from C2 to C30, preferably from C3 to C20 and most preferably from C4 to C18 in the substituent.

If the at least one mono-substituted succinic anhydride is provided in combination with at least one mono-substituted succinic acid, the at least one mono-substituted succinic acid is present in an amount of ≤10 mol.-%, based on the molar sum of the at least one mono-substituted succinic anhydride and the at least one mono-substituted succinic acid. For example, the at least one mono-substituted succinic acid is present in an amount of ≤5 mol.-%, preferably of ≤2.5 mol.-% and most preferably of ≤1 mol.-%, based on the molar sum of the at least one mono-substituted succinic anhydride and the at least one mono-substituted succinic acid.

In one embodiment of the present invention, at least one mono-substituted succinic anhydride and at least one mono-substituted succinic acid are provided in method step b).

If at least one mono-substituted succinic anhydride and at least one mono-substituted succinic acid are provided in method step b), the at least one mono-substituted succinic anhydride and the at least one mono-substituted succinic acid are preferably provided as a blend.

It is one requirement of the present invention that the at least one mono-substituted succinic anhydride and the optional at least one mono-substituted succinic acid are provided in a total amount of from 0.1 to 3 wt.-%, based on the total dry weight of the at least one calcium carbonate-containing filler material.

For example, the at least one mono-substituted succinic anhydride and the optional at least one mono-substituted succinic acid are provided in an amount of from 0.1 to 2.5 wt.-%, preferably in an amount of from 0.1 to 2 wt.-%, more preferably in an amount of from 0.1 to 1.5 wt.-%, even more preferably in an amount of from 0.1 to 1 wt.-% and most preferably in an amount of from 0.2 to 0.8 wt.-% based on the total dry weight of the at least one calcium carbonate-containing filler material.

Additionally or alternatively, the at least one mono-substituted succinic anhydride and the optional at least one mono-substituted succinic acid of the present invention are preferably provided in a quantity such that the total weight of said at least one mono-substituted succinic anhydride and the optional at least one mono-substituted succinic acid on the surface of the at least one calcium carbonate-containing filler material is less than 5 mg/m² of the at least one calcium carbonate-containing filler material provided in step (a).

In one embodiment of the present invention, the at least one mono-substituted succinic anhydride and the optional at least one mono-substituted succinic acid of the present invention are preferably provided in a quantity such that the total weight of said at least one mono-substituted succinic anhydride and mono-substituted succinic acid and/or salty reaction product(s) thereof on the surface of the at least one calcium carbonate-containing filler material is less than 4.5 mg/m² and most preferably less than 4.0 mg/m² of the at least one calcium carbonate-containing filler material provided in step (a).

For example, the at least one mono-substituted succinic anhydride and the optional at least one mono-substituted succinic acid of the present invention are preferably provided in a quantity such that the total weight of the at least one mono-substituted succinic anhydride and the optional at least one mono-substituted succinic acid on the surface of the surface treated filler material product is from 0.1 to 5 mg/m², more preferably from 0.2 to 4 mg/m² and most preferably from 1 to 4 mg/m² of the at least one calcium carbonate-containing filler material provided in step a).

Additionally or alternatively, it is to be noted that the at least one mono-substituted succinic anhydride and the optional at least one mono-substituted succinic acid of step (b) of the inventive process are provided as a liquid at room temperature, i.e. said at least one mono-substituted succinic anhydride features a viscosity of less than 5 000, preferably of less than 2 500, more preferably of less than 1.000 mPa·s and most preferably of less than 500 mPa·s at +20° C. (±2° C.), when measured with the appropriate equipment e.g. Physica MCR 300 rheometer (Paar Physica) equipped with the measuring cell TEZ 150 P-C and the CC 28.7 measuring system at a shear rate of 5 s$^{-1}$ and at +20° C. (±2° C.).

Characterization of Step c): Contacting of the at Least One Calcium Carbonate-Containing Filler Material with the at Least One Mono-Substituted Succinic Anhydride According to step c) of the inventive process, the at least one calcium carbonate-containing filler material of step a) is contacted under mixing, in one or more steps, with the at least one mono-substituted succinic anhydride and the optional at least one mono-substituted succinic acid of step b).

Step c) of contacting the at least one calcium carbonate-containing filler material with the at least one mono-substituted succinic anhydride and the optional at least one mono-substituted succinic acid takes place under mixing conditions. The skilled man will adapt these mixing conditions (such as the configuration of mixing pallets and mixing speed) according to his process equipment.

In one preferred embodiment of the present invention, the inventive process may be a continuous process. In this case, it is possible to contact the at least one calcium carbonate-containing filler material with the at least one mono-substituted succinic anhydride and the optional at least one mono-substituted succinic acid in a constant flow, so that a constant concentration of the at least one mono-substituted succinic anhydride and the optional at least one mono-substituted succinic acid is provided during step c).

Alternatively, the at least one calcium carbonate-containing filler material is contacted with the at least one mono-substituted succinic anhydride and the optional at least one mono-substituted succinic acid of step (b) in one step, wherein said at least one mono-substituted succinic anhydride and the optional at least one mono-substituted succinic acid is preferably added in one portion.

In another embodiment of the present invention, the inventive process may be a batch process, i.e. the at least one calcium carbonate-containing filler material is contacted with the at least one mono-substituted succinic anhydride and the optional at least one mono-substituted succinic acid in more than one steps, wherein said at least one mono-substituted succinic anhydride and the optional at least one mono-substituted succinic acid is preferably added in about equal portions. Alternatively, it is also possible to add the at least one mono-substituted succinic anhydride and the optional at least one mono-substituted succinic acid in unequal portions to the at least one calcium carbonate-containing filler material, i.e. in larger and smaller portions.

According to one embodiment of the present invention, contacting step (c) is carried out in a batch or continuous process for a period of time from 0.1 to 1000 s. For example, contacting step (c) is a continuous process and comprises one or several contacting steps and the total contacting time is from 0.1 to 20 s, preferably from 0.5 to 15 s and most preferably from 1 to 10 s.

When implementing the at least one mono-substituted succinic anhydride and the optional at least one mono-substituted succinic acid of step b), it features a workable viscosity at about room temperature, i.e. the at least one mono-substituted succinic anhydride and the optional at least one mono-substituted succinic acid is in a liquid state. Therefore, the contacting of the at least one calcium carbonate-containing filler material with the at least one mono-substituted succinic anhydride and the optional at least one mono-substituted succinic acid may be carried out at lower treatment temperatures than that used in processes implementing fatty acids and/or fatty acid salts having at least 10 chain carbon atoms. It is thus one requirement of the present invention that the temperature is adjusted during contacting step c) such that the at least one mono-substituted succinic anhydride and the optional at least one mono-substituted succinic acid is molten.

A "molten" or "liquid" state in the meaning of the present invention is defined as the state in which a material is entirely liquid, in other words is entirely melted. Whereas the phenomenon of melting occurs at constant temperature on application of energy, a substance is qualified as being molten as of the moment following melting when the temperature begins to rise, as observed on a curve plotting temperature versus energy input obtained by Dynamic Scanning calorimetry, DSC, (DIN 51005: 1983-11).

Accordingly, it is appreciated that the temperature before and/or during contacting step c) is adjusted such that the temperature is at least 2° C. above the melting point of the at least one mono-substituted succinic anhydride and the optional at least one mono-substituted succinic acid. For example, the temperature before contacting step c) is adjusted such that the temperature is at least 2° C. above the melting point of the at least one mono-substituted succinic anhydride and the optional at least one mono-substituted succinic acid. Alternatively, the temperature before and during contacting step c) is adjusted such that the temperature is at least 2° C. above the melting point of the at least one mono-substituted succinic anhydride and the optional at least one mono-substituted succinic acid.

It is appreciated that the wording "melting point of the at least one mono-substituted succinic anhydride and the optional at least one mono-substituted succinic acid" refers to the melting point of the at least one mono-substituted succinic anhydride or, if the at least one mono-substituted succinic acid is present, to the blend comprising the at least one mono-substituted succinic anhydride and the at least one mono-substituted succinic acid.

In one embodiment of the present invention, the temperature before and/or during contacting step c) is adjusted such that the temperature is at least 5° C., preferably, at least 8° C. and most preferably at least 10° C. above the melting point of the at least one mono-substituted succinic anhydride and the optional at least one mono-substituted succinic acid. For example, the temperature before and/or during contacting step c) is adjusted such that the temperature is from 2 to 50° C., preferably from 5 to 40° C., more preferably from 8 to 30° C. and most preferably from 10 to 20° C. above the melting point of the at least one mono-substituted succinic anhydride and the optional at least one mono-substituted succinic acid.

In one embodiment of the present invention, the contacting of the at least one calcium carbonate-containing filler material with the at least one mono-substituted succinic anhydride and the optional at least one mono-substituted succinic acid is thus carried out at a treatment temperature of below 200° C. For example, the contacting of at least one calcium carbonate-containing filler material with the at least one mono-substituted succinic anhydride and the optional at least one mono-substituted succinic acid is carried out at a treatment temperature of from 30 to 200° C., preferably of from 80 to 150° C. and most preferably of from 110 to 130° C.

The treatment time for carrying out the contacting of the at least one calcium carbonate-containing filler material with the at least one mono-substituted succinic anhydride and the optional at least one mono-substituted succinic acid of step (b) is carried out for a period of 1 000 s or less, preferably for a period of 500 s or less, more preferably for a period of 250 s or less and most preferably from 0.1 to 1 000 s. For example, contacting step (c) is carried out for a period of time from 0.1 to 20 s, preferably from 0.5 to 15 s and most preferably from 1 to 10 s. In general, the length of contacting the at least one calcium carbonate-containing filler material with the at least one mono-substituted succinic anhydride and the optional at least one mono-substituted succinic acid of step (b) is determined by the treatment temperature applied during said contacting. For example, where a treatment temperature of about 200° C. is applied, the treatment time is as short as, for example, about 0.1. If a treatment temperature of about 90° C. is applied, the treatment time can be as long as, for example, about 1 000 s.

It is appreciated that the at least one mono-substituted succinic anhydride and the optional at least one mono-substituted succinic acid are added in contacting step c) in an amount of from 0.1 to 2 wt.-%, based on the total dry weight of the at least one calcium carbonate-containing filler material of step a). For example, the at least one mono-substituted succinic anhydride and the optional at least one mono-substituted succinic acid is added in contacting step c) in an amount of from 0.2 to 1.5 wt.-% or of from 0.3 to 1 wt.-%, based on the total dry weight of the at least one calcium carbonate-containing filler material of step a).

In one embodiment of the present invention, the at least one calcium carbonate-containing filler material is preheated, i.e. activated, before contacting step c) is carried out. That is to say, the at least one calcium carbonate-containing filler material is treated at a temperature of from 50 to 200° C., preferably of from 80 to 200° C., more preferably of from 90 to 150° C. and most preferably of from 100 to 130° C. before contacting step c) is carried out.

The treatment time for carrying out the preheating of the at least one calcium carbonate-containing filler material is carried out for a period of 30 min or less, preferably for a period of 20 min or less and more preferably for a period of 15 min or less.

In one embodiment of the present invention, the preheating of the at least one calcium carbonate-containing filler material is carried out at a temperature that is of about equal to the temperature implemented during contacting step c).

The term "equal" temperature in the meaning of the present invention refers to a preheating temperature that is at most 20° C., preferably at most 15° C., more preferably 10° C. and most preferably at most 5° C. below or above the temperature implemented during contacting step c).

According to one embodiment of the present invention, the process further comprises step (d) of contacting the at least one calcium carbonate-containing filler material of step (a), in one or more steps, with at least one organic material such as polysiloxanes.

In case, the inventive process further comprises contacting step (d), such contacting of the at least one calcium carbonate-containing filler material with the at least one organic material may be carried out during and/or after the contacting of the at least one calcium carbonate-containing filler material with the at least one mono-substituted succinic anhydride and the optional at least one mono-substituted succinic acid of step (b). In one embodiment of the present invention, such contacting with the at least one organic material is carried out after the contacting of the at least one calcium carbonate-containing filler material with the at least one mono-substituted succinic anhydride and the optional at least one mono-substituted succinic acid of step (b). In this case, contacting step d) is preferably carried out at temperatures of from 40 to 200° C. For example, contacting step d) is carried out at temperatures of from 50 to 150° C. or from 60 to 120° C.

The at least one organic material such as polysiloxane is added in contacting step d) in an amount of from 100 to 1 000 ppm, preferably from 200 to 800 ppm and most preferably from 300 to 700 ppm, based on the total dry weight of the at least one calcium carbonate-containing filler material of step a)

Additionally or alternatively, the at least one organic material such as polysiloxane is preferably added such that the amount of the at least one organic material on the surface of the surface treated filler material product, i.e. in the treatment layer, is less than 0.1 mg, more preferably less than 0.08 mg and most preferably less than 0.07 mg of the total weight of the at least organic material/$m^2$ of the at least one calcium carbonate-containing filler material provided in step a).

The treatment time for carrying out the contacting of the at least one calcium carbonate-containing filler material with the at least one organic material is carried out for a period of 0.00166 to 166.66 min. For example, the contacting of the at least one calcium carbonate-containing filler material with the at least one organic material is carried out for a contacting time from 0.0166 to 20 min, preferably from 0.0833 to 15 min and most preferably from 0.166 to 10 min.

The length of contacting step d) is determined by the treatment temperature applied during said contacting. For example, where a treatment temperature of about 140° C. is applied, the treatment time is as short as, for example from about 0.166 to 1 min.

Thus, it is appreciated that the treatment layer formed on the surface of the at least one calcium carbonate-containing filler material comprises the at least one mono-substituted succinic anhydride provided in step b) and the optional at least one mono-substituted succinic acid, optionally provided in step b) and/or obtained as reaction product from contacting the calcium carbonate-containing filler material with the at least one mono-substituted succinic anhydride(s), and/or salty reaction product(s) thereof obtained from contacting the at least one calcium carbonate-containing filler material with the at least one mono-substituted succinic anhydride and the optional at least one mono-substituted succinic acid. In such a case, the treatment layer of the surface treated filler material product preferably comprises salty reaction product(s) of the mono-substituted succinic acid and/or the at least one mono-substituted succinic anhydride formed on the surface of said at least one calcium carbonate-containing filler material in step c). For example, salty reaction product(s) such as one or more calcium salts and/or magnesium salts of the at least one mono-substituted succinic acid and/or the at least one mono-substituted succinic anhydride. In one embodiment of the present invention, the treatment layer of the surface treated filler material product further comprises at least one organic material such as polysiloxane.

Thus, it is appreciated that the at least one calcium carbonate-containing filler material product obtained in process step c) and optionally after step d), i.e. the surface treated filler material product, comprises, preferably consists of, at least one calcium carbonate-containing filler material and a treatment layer comprising at least one mono-substituted succinic anhydride and at least one mono-substituted succinic acid and/or salty reaction product(s) thereof. The treatment layer is formed on the surface of said at least one calcium carbonate-containing filler material of step a).

In case the treatment layer on the surface of the at least one calcium carbonate-containing filler material comprises at least one mono-substituted succinic acid, it is preferred that the at least one mono-substituted succinic acid is formed from the applied at least one mono-substituted succinic anhydride. That is to say, the substituent of the at least one mono-substituted succinic acid and the substituent of the at least one mono-substituted succinic anhydride are the same.

Additionally or alternatively, the at least one mono-substituted succinic acid is provided in a blend together with the at least one mono-substituted succinic anhydride.

In one embodiment of the present invention, the treatment layer formed on the surface of the at least one calcium carbonate-containing filler material comprises the at least one mono-substituted succinic anhydride provided in step b) and at least one mono-substituted succinic acid or salty reaction product(s) thereof obtained from contacting the at least one calcium carbonate-containing filler material with the at least one mono-substituted succinic anhydride and the optional at least one mono-substituted succinic acid. Alternatively, the treatment layer formed on the surface of the at least one calcium carbonate-containing filler material comprises the at least one mono-substituted succinic anhydride provided in step b) and at least one mono-substituted succinic acid and salty reaction product(s) thereof obtained from contacting the at least one calcium carbonate-containing filler material with the at least one mono-substituted succinic anhydride and the optional at least one mono-substituted succinic acid.

The treatment layer is preferably characterized in that the total weight of the at least one mono-substituted succinic anhydride and at least one mono-substituted succinic acid and/or salty reaction product(s) thereof on the surface of the surface treated filler material product is from 0.1 to 5 mg/m$^2$, more preferably from 0.2 to 4 mg/m$^2$ and most preferably from 1 to 4 mg/m$^2$ of the at least one calcium carbonate-containing filler material provided in step a).

The treatment layer is preferably characterized in that the total weight of the at least one mono-substituted succinic anhydride and at least one mono-substituted succinic acid and/or salty reaction product(s) thereof on the surface of the surface treated filler material product is from 0.05 to 1 wt.-%/m$^2$, more preferably from 0.1 to 0.5 wt.-%/m$^2$ and most preferably from 0.15 to 0.25 wt.-%/m$^2$ of the at least one calcium carbonate-containing filler material provided in step a)

In one embodiment of the present invention, the treatment layer is characterized in that the total weight of the at least one mono-substituted succinic anhydride and mono-substituted succinic acid and/or salty reaction product(s) thereof and the optional at least one organic material on the surface of the surface treated filler material product is from 0.1 to 5 mg/m$^2$, more preferably from 0.25 to 4.5 mg/m$^2$ and most preferably from 1.0 to 4.0 mg/m$^2$ of the at least one calcium carbonate-containing material provided in step a).

Additionally or alternatively, the treatment layer of the surface treated filler material product comprises the at least one mono-substituted succinic anhydride and the at least one mono-substituted succinic acid and/or salty reaction product(s) thereof in a specific molar ratio. For example, the molar ratio of the at least one mono-substituted succinic anhydride and the at least one mono-substituted succinic acid to the salty reaction product(s) thereof is from 99.9:0.1 to 0.1:99.9, preferably from 70:30 to 90:10.

The wording "molar ratio of the at least one mono-substituted succinic anhydride and the at least one mono-substituted succinic acid to the salty reaction product(s) thereof" in the meaning of the present invention refers to the sum of the molecular weight of the at least one mono-substituted succinic anhydride and the sum of the molecular weight of the at least one mono-substituted succinic acid to the sum of the molecular weight of the mono-substituted succinic anhydride molecules in the salty reaction products thereof and the sum of the molecular weight of the mono-substituted succinic acid molecules in the salty reaction products thereof.

It is further appreciated that the obtained surface treated filler material product comprises the treatment layer in an amount of from 0.1 to 2.5 wt.-%, preferably in an amount of from 0.1 to 2 wt.-%, more preferably in an amount of from 0.1 to 1.5 wt.-%, even more preferably in an amount of from 0.1 to 1 wt.-% and most preferably in an amount of from 0.2 to 0.8 wt.-% based on the total dry weight of the at least one calcium carbonate-containing filler material.

The resulting surface treated filler material product obtained according to the present invention has excellent surface characteristics in comparison to mineral fillers treated with fatty acids and/or fatty acid salts having at least 10 chain carbon atoms, i.e. without the implementation of the at least one mono-substituted succinic anhydride and the optional at least one mono-substituted succinic acid.

In particular, it is appreciated that the surface treated filler material product obtained by the inventive process features a volatile onset temperature of ≥250° C. For example, the surface treated filler material product obtained by the inventive process features a volatile onset temperature of ≥260° C. or of ≥270° C.

Additionally or alternatively, the surface treated filler material product obtained by the inventive process features a total volatiles between 25 and 350° C. of less than 0.25%, and preferably of less than 0.23% by mass, e.g. of from 0.04 to 0.21% by mass, preferably from 0.08 to 0.15% by mass, more preferably from 0.1 to 0.12% by mass.

Furthermore, the surface treated filler material product obtained by the inventive process features a low moisture pick up susceptibility. It is preferred that the moisture pick up susceptibility of the surface treated filler material product obtained by the inventive process is such that its total surface moisture level is less than 0.8 mg/g of dry calcium carbonate-containing filler material, at a temperature of about +23° C. (±2° C.). For example, the surface treated filler material product obtained by the inventive process has a moisture pick up susceptibility of from 0.1 to 0.8 mg/g, more preferably of from 0.2 to 0.7 mg/g and most preferably of from 0.2 to 0.6 mg/g of dry calcium carbonate-containing material after at a temperature of +23 C (±2° C.).

Additionally or alternatively, the surface treated filler material product obtained by the inventive process has a hydrophilicity of below 8:2 volumetric ratio of water:ethanol measured at +23° C. (±2° C.) with the sedimentation method. For example, the surface treated filler material product has a hydrophilicity of below 7:3 volumetric ratio of water:ethanol measured at +23° C. (±2° C.) with the sedimentation method.

In view of the very good results obtained, one aspect of the present invention relates to the surface treated filler material product comprising a) at least one calcium carbonate-containing filler material having
   i) a weight median particle size $d_{50}$ value in the range from 0.1 μm to 7 μm, ii) a top cut $(d_{98})≤15$ μm,
   iii) a specific surface area (BET) of from 0.5 to 150 m²/g as measured by the BET nitrogen method, and
   iv) a residual total moisture content of ≤1 wt.-%, based on the total dry weight of the at least one calcium carbonate-containing filler material, and
b) a treatment layer on the surface of the at least one calcium carbonate-containing filler material comprising at least one mono-substituted succinic anhydride and at least one mono-substituted succinic acid and/or salty reaction product(s) thereof,
wherein the surface treated filler material product comprises the treatment layer in an amount of from 0.1 to 3 wt.-%, based on the total dry weight of the at least one calcium carbonate-containing filler material.

In one embodiment of the present invention, the surface treated filler material product is obtainable by the process of the present invention.

With regard to the definition of the at least one calcium carbonate-containing filler material, the at least one mono-substituted succinic anhydride, the at least one mono-substituted succinic acid, the salty reaction product(s) thereof, the surface treated filler material product, and preferred embodiments thereof, reference is made to the comments provided above when discussing process steps a), b) and c), and optional step d).

The surface treated filler material product is thus obtained is advantageously implemented in polymer composition comprising at least one polymeric resin and from 1 to 85 wt.-% of the surface treated filler material product.

Accordingly, the polymer composition comprises at least one polymeric resin. The polymer resin represents the backbone of the composition and provides strength, flexibility, toughness and durability to the final fiber and/or filament and/or film and/or thread.

It is appreciated that the at least one polymeric resin according to the present invention is not restricted to a specific resin material as long as the polymer composition is suitable for the preparation of fibers and/or filaments and/or films and/or thread.

In one embodiment of the present invention, the at least one polymeric resin is at least one thermoplastic polymer. Thus, it is preferred that the at least one polymeric resin is a thermoplastic polymer selected from the group comprising homopolymers and/or copolymers of polyolefins, polyamides, halogen-containing polymers and/or polyesters.

For example, if the at least one polymeric resin is a polyamide the at least one polymeric resin is preferably nylon.

Additionally or alternatively, the at least one polymeric resin is a homopolymer and/or copolymer of a polyolefin. For example, the at least one polymeric resin is a homopolymer and a copolymer of a polyolefin. Alternatively, the at least one polymeric resin is a homopolymer or a copolymer of a polyolefin.

It is appreciated that the at least one polymeric resin is preferably a homopolymer of a polyolefin.

For example, the polyolefin can be polyethylene and/or polypropylene and/or polybutylene. Accordingly, if the polyolefin is polyethylene, the polyolefin is selected from the group comprising homopolymers and/or copolymers of polyethylene like high-density polyethylene (HDPE), medium-density polyethylene (MDPE), low-density polyethylene (LDPE), very low-density polyethylene (VLDPE), linear low-density polyethylene (LLDPE).

For example, the polyolefin is a homopolymer and/or copolymer of polyethylene.

The expression homopolymer of polyethylene used in the present invention relates to polyethylene comprising a polyethylene that consists substantially, i.e. of more than 99.7 wt.-%, still more preferably of at least 99.8 wt.-%, based on the total weight of the polyethylene, of ethylene units. For example, only ethylene units in the homopolymer of polyethylene are detectable.

In case the at least one polymeric resin of the polymer composition comprises a copolymer of polyethylene, it is appreciated that the polyethylene contains units derivable from ethylene as major components. Accordingly, the copolymer of polyethylene comprises at least 55 wt.-% units derivable from ethylene, more preferably at least 60 wt.-% of units derived from ethylene, based on the total weight of the polyethylene. For example, the copolymer of polyethylene comprises 60 to 99.5 wt.-%, more preferably 90 to 99 wt.-%, units derivable from ethylene, based on the total weight of the polyethylene. The comonomers present in such copolymer of polyethylene are $C_3$ to $C_{10}$ α-olefins, preferably 1-butene, 1-hexene and 1-octene, the latter especially preferred.

Additionally or alternatively, the polyolefin is a homopolymer and/or copolymer of polypropylene.

The expression homopolymer of polypropylene as used throughout the instant invention relates to a polypropylene that consists substantially, i.e. of more than 99 wt.-%, still more preferably of at least 99.5 wt.-%, like of at least 99.8 wt.-%, based on the total weight of the polypropylene, of propylene units. In a preferred embodiment only propylene units are detectable in the homopolymer of polypropylene.

In case the at least one polymeric resin of the polymer composition comprises a copolymer of polypropylene, the polypropylene preferably contains units derivable from propylene as major components. The copolymer of polypropylene preferably comprises, preferably consists of, units derived from propylene and $C_2$ and/or at least one $C_4$ to $C_{10}$ α-olefin. In one embodiment of the present invention, the copolymer of polypropylene comprises, preferably consists of, units derived from propylene and at least one α-olefin selected from the group consisting of ethylene, 1-butene, 1-pentene, 1-hexene and 1-octene. For example, the copolymer of polypropylene comprises, preferably consists of, units derived from propylene and ethylene. In one embodiment of the present invention, the units derivable from propylene constitutes the main part of the polypropylene, i.e. at least 60 wt.-%, preferably of at least 70 wt.-%, more preferably of at least 80 wt.-%, still more preferably of from 60 to 99 wt.-%, yet more preferably of from 70 to 99 wt.-% and most preferably of from 80 to 99 wt.-%, based on the total weight of the polypropylene. The amount of units derived from $C_2$ and/or at least one $C_4$ to $C_{10}$ α-olefin in the copolymer of polypropylene, is in the range of 1 to 40 wt.-%, more preferably in the range of 1 to 30 wt.-% and most preferably in the range of 1 to 20 wt.-%, based on the total weight of the copolymer of polypropylene.

If the copolymer of polypropylene comprises only units derivable from propylene and ethylene, the amount of ethylene is preferably in the range of 1 to 20 wt.-%, preferably in the range of 1 to 15 wt.-% and most preferably in the range of 1 to 10 wt.-%, based on the total weight of the copolymer of polypropylene. Accordingly, the amount of propylene is preferably in the range of 80 to 99 wt.-%, preferably in the range of 85 to 99 wt.-% and most preferably in the range of 90 to 99 wt.-%, based on the total weight of the copolymer of polypropylene.

Additionally or alternatively, the polyolefin is a homopolymer and/or copolymer of polybutylene.

The expression homopolymer of polybutylene as used throughout the instant invention relates to a polybutylene that consists substantially, i.e. of more than 99 wt.-%, still more preferably of at least 99.5 wt.-%, like of at least 99.8 wt.-%, based on the total weight of the polybutylene, of butylene units. In a preferred embodiment only butylene units are detectable in the homopolymer of polybutylene.

In case the at least one polymeric resin of the polymer composition comprises a copolymer of polybutylene, the polybutylene preferably contains units derivable from butylene as major components. The copolymer of polybutylene preferably comprises, preferably consists of, units derived from butylene and $C_2$ and/or $C_3$ and/or at least one $C_5$ to $C_{10}$ α-olefin. In one embodiment of the present invention, the copolymer of polybutylene comprises, preferably consists of, units derived from butylene and at least one α-olefin selected from the group consisting of ethylene, 1-propene, 1-pentene, 1-hexene and 1-octene. For example, the copolymer of polybutylene comprises, preferably consists of, units derived from butylene and ethylene. In one embodiment of the present invention, the units derivable from butylene constitutes the main part of the polybutylene, i.e. at least 60 wt.-%, preferably of at least 70 wt.-%, more preferably of at least 80 wt.-%, still more preferably of from 60 to 99 wt.-%, yet more preferably of from 70 to 99 wt.-% and most preferably of from 80 to 99 wt.-%, based on the total weight of the polybutylene. The amount of units derived from $C_2$ and/or $C_3$ and/or at least one $C_5$ to $C_{10}$ α-olefin in the copolymer of polybutylene, is in the range of 1 to 40 wt.-%, more preferably in the range of 1 to 30 wt.-% and most preferably in the range of 1 to 20 wt.-%, based on the total weight of the copolymer of polybutylene.

If the at least one polymeric resin is a homopolymer and/or copolymer of a halogen-containing polymer, the at least one polymeric resin is preferably selected from polyvinylchloride (PVC), polyvinylidene chloride (PVDC), polyvinylidene fluoride (PVDF) and polytetrafluoroethylene (PTFE).

If the at least one polymeric resin is a homopolymer and/or copolymer of polyester, the at least one polymeric resin is preferably selected from polyethylene terephthalate (PET), polytrimethylene terephthalate (PTT), polybutylene terephthalate (PBT), polyethylene aphthalate (PEN), but also degradable polyesters, such as polylactic acid (polylactide, PLA).

In one embodiment of the present invention, the at least one polymeric resin is a homopolymer of polyethylene and/or polypropylene and/or polybutylene. For example, the at least one polymeric resin is a homopolymer of polyethylene and polypropylene. Alternatively, the at least one polymeric resin is a homopolymer of polyethylene or polypropylene. In one embodiment of the present invention, the at least one polymeric resin is a homopolymer of polypropylene.

The expression "at least one" polymeric resin means that one or more kinds of polymeric resin may be present in the inventive polymer composition.

Full or partially based bio-based polymers are derived from renewable biomass sources, such as vegetable fats and oils, corn starch, pea starch or microbiota, aliphatic biopolyesters such as polyhydroxyalkanoates (PHA), polyhydroxybutyrate (PHB), polyhydroxyvalerate (PHV), polyhydroxyhexanoate (PHH), or polyesters such as polyethylene terephthalate (PET).

Blends, Mixtures, Alloys and combinations of two or more of the above mentioned polymers can be used as well in the present invention.

Accordingly, it is appreciated that the at least one polymeric resin may be a mixture of two or more kinds of polymeric resins. For example, if the at least one polymeric resin is a mixture of two or more polymeric resins, one polymeric resin is a homopolymer or copolymer of polypropylene, while the second or further polymeric resin is selected from the group comprising homopolymers and/or copolymers of polyethylene, polybutylene, polyamides, polyesters, halogen-containing polymers and mixtures thereof, wherein the polymers can be fully or partially based biopolymers.

In one embodiment of the present invention, the at least one polymeric resin is one kind of polymeric resin. Preferably, the at least one polymeric resin is a homopolymer of polyethylene or polypropylene.

In one embodiment of the present invention, the at least one polymeric resin has a melting temperature Tm of above 100° C., more preferably of above 150° C., like of above 200° C. For example, the melting temperature of the at least one polymeric resin ranges from 100 to 350° C., more preferably ranges from 150 to 325° C. and most preferably ranges from 200 to 300° C.

Furthermore, it is appreciated that the at least one polymeric resin may be selected from polymeric resins having a broad spectrum of melt flow rate. In general, it is preferred that the at least one polymeric resin has a melt flow rate MFR (190° C.) of from 0.1 to 3 000 g/10 min, more preferably of from 0.2 to 2 500 g/10 min. For example, the at least one polymeric resin has a melt flow rate MFR (190° C.) of from 0.3 to 2 000 g/10 min or from 0.3 to 1 600 g/10 min. Additionally or alternatively, the at least one polymeric resin has a melt flow rate MFR (230° C.) of from 0.1 to 3 000 g/10 min, more preferably of from 0.2 to 2 500 g/10 min. For example, the at least one polymeric resin has a melt flow rate MFR (230° C.) of from 0.3 to 2 000 g/10 min or from 0.3 to 1 600 g/10 min.

For example, if the at least one polymeric resin is a polyolefin being a homopolymer and/or copolymer of polypropylene, it is preferred that the at least one polymeric resin has a melt flow rate MFR (190° C., 2.16 kg) of from 1 to 3 000 g/10 min, more preferably of from 3 to 2 500 g/10 min. For example, the at least one polymeric resin which is a homopolymer and/or copolymer of polypropylene has a melt flow rate MFR (190° C.) of from 5 to 2 000 g/10 min or from 10 to 1 600 g/10 min. It is preferred that the at least one polymeric resin which is a homopolymer and/or copolymer of polypropylene has a melt flow rate MFR (230° C.) of from 1 to 3 000 g/10 min, more preferably of from 3 to 2 500 g/10 min. For example, the at least one polymeric resin which is a homopolymer and/or copolymer of polypropylene has a melt flow rate MFR (230° C.) of from 5 to 2 000 g/10 min or from 10 to 1 600 g/10 min.

If the at least one polymeric resin is a polyolefin being a homopolymer and/or copolymer of polyethylene, it is appreciated that the at least one polymeric resin has a rather low melt flow rate. Accordingly, it is preferred that the at least one polymeric resin which is a homopolymer and/or copolymer of polyethylene has a melt flow rate MFR (190° C.) of from 0.5 to 20 g/10 min, more preferably of from 0.7 to 15 g/10 min. For example, the at least one polymeric resin has a melt flow rate MFR (190° C.) of from 0.9 to 10 g/10 min or from 0.9 to 5 g/10 min. Additionally or alternatively, the at least one polymeric resin which is a homopolymer and/or copolymer of polyethylene has a melt flow rate MFR (230° C.) of from 0.1 to 3 000 g/10 min, more preferably of from 0.2 to 2 500 g/10 min. For example, the at least one polymeric resin which is a homopolymer and/or copolymer of polyethylene has a melt flow rate MFR (230° C.) of from 0.3 to 2 000 g/10 min or from 0.3 to 1 600 g/10 min.

A further essential component of the present polymer composition is the surface treated filler material product. With regard to the definition of the surface treated filler material product and preferred embodiments thereof, reference is made to the comments provided above when discussing process steps a), b) and c).

It is one requirement of the present invention that the polymer composition comprises the surface treated filler material product in an amount of 1 to 85 wt.-%, based on the total weight of the polymer composition.

In one embodiment of the present invention, the polymer composition comprises the surface treated filler material product in an amount of from 5 to 85 wt.-% and preferably from 10 to 85 wt.-%, based on the total weight of the polymer composition. For example, the polymer composition comprises the surface treated filler material product in an amount of from 15 to 80 wt.-%, based on the total weight of the polymer composition.

In one embodiment of the present invention, the polymer composition is a masterbatch.

The term "masterbatch" refers to a composition having a concentration of the surface treated filler material product that is higher than the concentration of the polymer composition used for preparing the final application product such as a fiber and/or filament and/or film. That is to say, the masterbatch is further diluted such as to obtain a polymer composition which is suitable for preparing the final application product such as a fiber and/or filament and/or film and/or thread.

For example, the masterbatch comprises the surface treated filler material product in an amount of from 50 to 85 wt.-%, preferably from 60 to 85 wt.-% and more preferably from 70 to 80 wt.-%, based on the total weight of the masterbatch.

According to one embodiment of the present invention, the masterbatch is used to produce fibers and/or filaments and/or films and/or threads.

According to a further embodiment, the polymer masterbatch obtainable by the inventive process may be used in the manufacture of polymer products, wherein said polymer products preferably comprise polyolefin articles, such as woven fibers, nonwoven fibers, profiles, cables, films, or molded products.

The products comprising the polymer masterbatch according to the present invention may be manufactured by any process known to the skilled person.

In the art, many methods for the manufacture of polymer products are known. These methods include, without being limited to, melt processing techniques, for example, profile extrusion (for pipes, sheets and hollow sheets), cable extrusion, film extrusion (for cast films and blown films), molding (e.g., injection molding, rotomolding, blow molding and thermoforming), fiber spinning (e.g., melt spinning, wet spinning, dry spinning and structural fibers), co-kneading and pultrusion. The final articles may provide mono-layer or multi-layer structures.

According to one embodiment of the present invention, the polymer masterbatch obtainable by the inventive process can advantageously be used for the preparation of various shaped articles for plastics applications. Examples include flexible packaging for industrial and consumer applications, including roll stocks, bags, pouches, labels, wraps, lidding, shrink sleeves and stretch films; rigid packaging for industrial and consumer applications including plastic bottles, cups and containers; building and construction materials, including pipes and conduits, cladding and profiles, insulation, seals and gaskets, geotextiles; agriculture and horticulture materials including greenhouse material, mulch films, tunnel, silage, bale wraps, boxes and crates; transportation and automotive applications including interior parts, such as instrument and door panels, consoles, pillars and seating; exterior parts, such as bumper fascia, fenders, tailgates as well as under the hood applications including air ducts, air intake manifolds, radiators and cooling hoses; electrical and electronic applications including CD players, DVD systems, personal computers and TV sets, notebooks, tablets, smartphones, cookers, refrigerators and freezers, washing machines, dishwashers, tools and office equipment; medical and health applications including disposable caps, gowns, masks, scrub suits and shoe covers, drapes, wraps and packs, sponges, dressings and wipes, bed linen, contamination control gowns, examination gowns, lab coats, isolation gowns, diagnostic medical machinery and medical devices; personal care products including absorbent hygiene products (AHP), baby diapers, feminine hygiene products and adult incontinence products, wipes, skin care products, depilatory strips; household and furniture products, including wood composites, decorative foils, floor coverings, flooring, kitchen ware, cleaners, pet care, lawn and garden articles; toys, sports and leisure articles including playhouses, building kits, play vehicles, sports and fitness devices, shoes, clothing and sportswear, safety equipment (helmets, kneepads), sports equipment, and suit cases.

In another embodiment of the present invention, the polymer composition used for preparing the final application product such as a fiber and/or filament and/or film and/or thread comprises the surface treated filler material product in an amount of from 1 to 50 wt.-%, preferably of from 5 to 45 wt.-% and most preferably from 10 to 40 wt.-%, based on the total weight of the polymer composition. For example, the polymer composition used for preparing the final application product such as a fiber and/or filament and/or film comprises the surface treated filler material product in an amount of from 15 to 25 wt.-%, based on the total weight of the polymer composition.

In another embodiment of the present invention, the polymer composition used for preparing the final application product such as a fiber and/or filament and/or film and/or thread comprises the at least one calcium carbonate-containing material in an amount of from 1 and 10 wt.-%, based on the total weight of the polymer composition. It is appreciated that the polymer composition preferably comprises this amount when it is used as packaging material for acidic food like citrus fruits or containers and/or bottles for fruit juice.

If a masterbatch is used to produce fibers and/or filaments and/or films and/or threads, it is preferred that the masterbatch is diluted such as to obtain a polymer composition suitable for preparing the final application product such as a fiber and/or filament and/or film and/or thread. That is to say, the masterbatch is diluted such as to comprises the surface treated filler material product in an amount of from 1 to 50 wt.-%, preferably of from 5 to 45 wt.-% and most preferably from 10 to 40 wt.-%, based on the total weight of the polymer composition.

A filter pressure test was performed in order to determine the filter pressure value FPV of a LLDPE masterbatch as described above and compared to the FPV a masterbatch comprising a mineral material of the prior art.

The filter pressure test as herein described provides for the Filter Pressure Value, in the present case, of dispersed mineral material in a LLDPE. The Filter Pressure Value FPV is defined as the increase of pressure per gram filler. This test is performed to determine the dispersion quality and/or presence of excessively coarse particles or agglomerates of mineral materials in a masterbatch. Low Filter Pressure Values refers to a good dispersion and fine material, wherein high Filter Pressure Values refer to bad dispersion and coarse or agglomerated material.

The Filter Pressure test was performed on a commercially available Collin Pressure Filter Test, Teach-Line FT-E20T-IS, according to the standard EN 13900-5. Filter type used was 14 μm and 25 μm, extrusion was carried out at 200° C.

According to another embodiment of the present invention, the polymer composition is a fibre and/or filament and/or film and/or thread. For example, the fiber and/or filament and/or film and/or thread comprises the surface treated filler material product in an amount of from 1 to 50 wt.-%, preferably from 5 to 45 wt.-%, more preferably from 10 to 40 wt.-% and most preferably from 15 to 25 wt.-%, based on the total weight of the fiber and/or filament and/or film and/or thread.

The surface treated filler material product according to the present invention imparts excellent mechanical properties to final application products such as fibers and/or filaments and/or films and/or threads. In particular, the surface treated filler material product imparts excellent mechanical properties to final application products such as fibers and/or filaments and/or films and/or threads, when the surface treated filler material product is provided in form of the polymer composition of the present invention.

Thus, the present invention refers in a further aspect to a fibre and/or filament and/or film and/or threads comprising the polymer composition as defined above and/or the surface treated filler material product as defined above.

Furthermore, the present invention refers in another aspect to a method for preparing a fibre and/or filament and/or film and/or thread, the method comprising at least the steps of:
 a) providing the polymer composition as defined above, and
 b) subjecting the polymer composition of step a) to conditions under which said polymer composition is converted into a fibre and/or filament and/or film and/or thread.

Appropriate method conditions for preparing fibres and/or filaments and/or films and/or threads are commonly known to the skilled person and/or can be established by routine modifications based on common general knowledge.

For example, the polymer composition of the present invention may advantageously be implemented in a process of mixing and/or extruding and/or compounding and/or blow moulding for preparing fibers and/or filaments and/or films and/or threads, wherein the at least one polymeric resin is preferably a thermoplastic polymer selected from the group comprising homopolymers and/or copolymers of polyolefins, polyamides and/or polyesters.

The term "fiber" in the meaning of the present invention refers to a linear structure forming textile fabrics such as nonwovens which typically consist of fiber webs bonded together by e.g. mechanical methods. Accordingly, the term "fiber" is understood to refer to a finite structure.

The term "thread" in the meaning of the present invention refers to a linear structure forming textile fabrics such as nonwovens which typically consist of thread webs bonded together by e.g. mechanical methods. Accordingly, the term "thread" is understood to refer to a finite structure. The thread may be constructed as mono-, bi- or multi-thread. If a bi- or multi-thread is present, the composition of the single thread may be substantially the same. That is to say, the compositions of the single threads comprise substantially the same components, i.e. the at least one polymeric resin and surface treated filler material product, in the same amounts. Alternatively, the composition of the single threads may be different. That is to say, the compositions of the single threads may comprise the same components, i.e. the at least one polymeric resin and surface treated filler material product, in varying amounts or the compositions of the single threads may comprise different components, i.e. the at least one polymeric resin and/or surface treated filler material product may be different, in the same amounts or the composition of the single threads may comprise different components, i.e. the at least one polymeric resin and/surface treated filler material product may be different may be different, in varying amounts.

The term "filament" in the meaning of the present invention refers to a structure that differs from fibers by its structure length. Accordingly, the term "filament" is understood to refer to endless fibers. It is further appreciated that the filament may be constructed as mono-, bi- or multi-filament. If a bi- or multi-filament is present, the composition of the single filaments may be substantially the same. That is to say, the compositions of the single filaments comprise substantially the same components, i.e. the at least one polymeric resin and surface treated filler material product, in the same amounts. Alternatively, the composition of the single filaments may be different. That is to say, the compositions of the single filaments may comprise the same components, i.e. the at least one polymeric resin and surface treated filler material product, in varying amounts or the compositions of the single filaments may comprise different components, i.e. the at least one polymeric resin and/or surface treated filler material product may be different, in the same amounts or the composition of the single filaments may comprise different components, i.e. the at least one polymeric resin and/or surface treated filler material product may be different may be different, in varying amounts.

The cross-section of the filaments and/or fibers and/or threads may have a great variety of shapes. It is preferred that the cross-sectional shape of the filaments and/or fibers and/or threads may be round, oval or n-gonal, wherein n is ≥3, e.g. n is 3. For example, the cross-sectional shape of the filaments and/or fibers and/or threads is round or trilobal, like round. Additionally or alternatively, the cross-sectional shape of the filaments and/or fibers and/or threads is hollow.

It is appreciated that the filaments and/or fibers and/or threads may be prepared by all techniques known in the art used for preparing such filaments and/or fibers and/or threads. For example, the filaments and/or fibers and/or threads of the present invention can be prepared by the well known melt-blown process, spunbonded process or staple fibre production.

Further to this, said filled PP masterbatches were used by melt extrusion processes to form fiber and filaments and continuous filament nonwoven fabrics by means known to the skilled person.

In accordance with known technology such as the continuous filament spinning for yarn or staple fiber, and nonwoven processes such as spunbond production and meltblown production, the fibers and filaments are formed by extrusion of the molten polymer through small orifices. In general, the fibers or filaments thus formed are then drawn or elongated to induce molecular orientation and affect crystallinity, resulting in a reduction in diameter and an improvement in physical properties. Spunmelt is a generic term describing the manufacturing of nonwoven webs (fabrics) directly from thermoplastic polymers. It encompasses 2 processes (spunlaid and meltblown) and the combination of both.

In this process polymer granules are melted and molten polymer is extruded through a spinneret assembly which creates a plurality of continuous polymeric filaments. The filaments are then quenched and drawn, and collected to form a nonwoven web. Some remaining temperature can cause filaments to adhere to one another, but this cannot be regarded as the principal method of bonding. There are several methods available for forming the collected web of continuous filaments into a useful product by a bonding step, which includes, but is not be limited to calendaring, hydroentangling,
needling and/or bonding by means of chemicals or adhesives.

The spunlaid process (also known as spunbonded) has the advantage of giving nonwovens greater strength. Co-extrusion of second components is used in several spunlaid processes, usually to provide extra properties or bonding capabilities. In meltblown web formation, low viscosity polymers are extruded into a high velocity airstream on leaving the spinneret. This scatters the melt, solidifies it and breaks it up into a fibrous web.

It is known to those skilled in the art to combine processes or the fabrics from different processes to produce composite fabrics which possess certain desirable characteristics. Examples of this are combining spunbond and meltblown to produce a laminate fabric that is best known as SMS, meant to represent two outer layers of spunbond fabric and an inner layer of meltblown fabric. Additionally either or both of these processes may be combined in any arrangement with a staple fiber carding process or bonded fabrics resulting from a nonwoven staple fiber carding process. In such described laminate fabrics, the layers are generally at least partially consolidated by one of the bonding steps listed above.

Processes are well known in the art, and are commercially available, for producing spunbond fabric of polypropylene polymeric resin. The two typical processes are known as the Lurgi process and the Reifenhäuser process.

The Lurgi process is based on the extrusion of molten polymer through spinneret orifices followed by the newly formed extruded filaments being quenched with air and drawn by suction through Venturi tubes. Subsequent to formation, the filaments are disbursed on a conveyor belt to form a nonwoven web.

The Reifenhäuser process differs from the Lurgi process in that the quenching area for the filaments is sealed, and the quenched air stream is accelerated, thus inducing more effective entrainment of the filaments into the air stream.

In the above-described systems, nonwoven fabrics are generally produced using polypropylene resins having a melt flow index of about 25 to 40 grams/10 minutes. A Lurgi line was used to produce polypropylene nonwovens. Extruder temperatures are between 230° and 250° C. The four spin beams are equipped with melt pumps and spinnerets which contain 600 orifices each with a diameter of 0.8 millimeters. The extruded filaments are formed to a nonwoven web. The conveyor belt speed was adjusted to 20 meters/minute and hydroentangling was used to bond the nonwoven web. Hydroentangling, also known as spunlacing, is a process which employs high pressure water jets to entangle fibers in a loose web thereby creating a fabric held together by frictional forces between the said fibers. The final bonded nonwoven web with a width of 100 cm has a fabric weight of 385 g/m2.

Samples of the said nonwoven fabrics comprising the CaCO3 according to the present invention and samples of nonwoven fabrics comprising the prior art CaCO3 are compared hereafter in tables 5 and 6. Different amounts of the filled masterbatches were mixed with further polypropylene (PP HF420FB, a homo-polypropylene with MFR 19 g/10 min. (230° C., 2.16 kg, ISO 1133) from *Borealis*) and nonwoven fabrics were made from these mixtures.

The term "film" in the meaning of the present invention refers to a structure that differs from filaments and/or fibers by its dimensional structure. Accordingly, the term "film" is understood to refer to a sheet.

It is appreciated that the films may be prepared by all techniques known in the art used for preparing such films. For example, the films of the present invention can be prepared by the well known techniques used for preparing stretched/oriented films, and preferably extrusion coating films, blown films, technical blown films, monotapes, cast films and the like.

Accordingly, fibers and/or filaments and/or films and/or threads according to the present invention are characterized in that they contain said polymer composition and/or surface treated filler material product and in that they have improved material properties such as improved mechanical properties.

As another advantage, fibers and/or filaments and/or films and/or threads according to the present invention cause lower pressure decreases during film extrusion. In addition thereto, the fibers and/or filaments and/or films and/or threads according to the present invention further show good mechanical properties such as tensile modulus, tensile test at yield and at break, elongation at break and tear resistance.

In view of the very good results obtained with regard to the hydrophilicity of the surface treated filler material product treated with at least one mono-substituted succinic anhydride, as defined above, a further aspect of the present invention is directed to the use of the mono-substituted succinic anhydride for decreasing the hydrophilicity of a calcium carbonate-containing filler material surface. In particular, the at least one mono-substituted succinic anhydride as defined above can be used to decrease the hydrophilicity of the calcium carbonate-containing filler material surface such that the surface treated filler material product is suitable for use in fibers and/or filaments and/or films and/or threads. A still further aspect of the present invention is directed to the use of the surface treated filler material product, as defined above, for initiating the crosslinking reaction in epoxide resins.

Another aspect of the present invention is directed to an article comprising the polymer composition as defined above and/or the surface treated filler material product as defined above and/or the fibre and/or filament and/or film and/or thread as defined above. The article is preferably selected from the group comprising hygiene products, medical and healthcare products, filter products, geotextile products, agriculture and horticulture products, clothing, footwear and baggage products, household and industrial products, packaging products, construction products and the like.

Preferably, the hygiene products are selected from the group comprising absorbent hygiene products such as baby diapers or nappies, feminine hygiene, adult incontinence products, depilatory strips, bandages and wound dressings, disposable bath and face towels, disposable slippers and footwear, top sheets or coverstocks, consumer face masks, leg cuffs, acquisition/distribution layers, core wraps, back sheets, stretch ears, landing zones, dusting layers and fastening systems; and wipes such as wet wipes, skin care wipes, baby wipes, facial wipes, cleansing wipes, hand and body wipes, moist towelettes, personal hygiene wipes, feminine hygiene wipes, antibacterial wipes and medicated wipes.

Preferably, the medical and healthcare products are selected from the group comprising medical products which can be sterilized, medical packaging, caps like surgical disposable caps, protective clothing, surgical gowns, surgical masks and face masks, surgical scrub suits, surgical covers, surgical drapes, wraps, packs, sponges, dressings, wipes, bed linen, contamination control gowns, examination gowns, lab coats, isolation gowns, transdermal drug delivery, shrouds, underpads, procedure packs, heat packs, ostomy bag liners, fixation tapes, incubator mattress, sterilisation wraps (CSR wrap), wound care, cold/heat packs, drug delivery systems like patches.

Preferably, the filter products are selected from the group comprising gasoline filters, oil filters, air filters, water filters, coffee filters, tea bags, pharmaceutical industry filters, mineral processing filters, liquid cartridge and bag filters, vacuum bags, allergen membranes and laminates with non-woven layers.

Preferably, the geotextile products are selected from the group comprising soil stabilizers and roadway underlayment, foundation stabilizers, erosion control, canals construction, drainage systems, geomembrane protection, frost protection, agriculture mulch, pond and canal water barriers, sand infiltration barrier for drainage tile and landfill liners.

Preferably, the agriculture and horticulture products are selected from the group comprising crop covers, plant protection, seed blankets, weed control fabrics, greenhouse shading, root control bags, biodegradable plant pots, capillary matting, and landscape fabric.

Preferably, the clothing, footwear and baggage products are selected from the group comprising interlinings like fronts of overcoats, collars, facings, waistbands, lapels etc., disposable underwear, shoe components like shoelace eyelet reinforcement, athletic shoe and sandal reinforcement and inner sole lining etc., bag components, bonding agents, composition and (wash) care labels.

Preferably, the packaging products are selected from the group comprising interlinings like desiccant packaging, sorbents packaging, gift boxes, file boxes, nonwoven bags, book covers, mailing envelopes, Express envelopes, courier bags and the like.

Preferably, the household and industrial products are selected from the group comprising abrasives, bed linen like pocket cloth for pocket springs, separation layer, spring cover, top cover, quilt backing, duvet coverings, pillow cases etc., blinds/curtains, carpet/carpet backings like scatter rugs, carpet tiles, bath mats etc., covering and separation material, detergent pouches, fabric softener sheets, flooring, furniture/upholstery like inside lining, reverse fabric for cushions, dust cover, spring covering, pull strips etc., mops, table linen, tea and coffee bags, vacuum cleaning bags, wall-covering, wipes like household care wipes, floor care wipes, cleaning wipes, pet care wipes etc., automotive building, cable wrapping, civil engineering, filtration packaging, protective clothing, primary and secondary carpet backing, composites, marine sail laminates, tablecover laminates, chopped strand mats, backing/stabilizer for machine embroidery, packaging where porosity is needed, insulation like fiberglass batting, pillows, cushions, padding like upholstery padding, batting in quilts or comforters, consumer and medical face masks, mailing envelopes, tarps, tenting and transportation (lumber, steel) wrapping, disposable clothing like foot coverings and coveralls, and weather resistant house wraps.

Preferably, the construction products are selected from the group comprising house wrap, asphalt overlay, road and railroad beds, golf and tennis courts, wallcovering backings, acoustical wall coverings, roofing materials and tile underlayment, soil stabilizers and roadway underlayment, foundation stabilizers, erosion control, canals construction, drainage systems, geomembrane protection, frost protection, agriculture mulch, pond and canal water barriers, and sand infiltration barriers for drainage tile.

Figure 1:
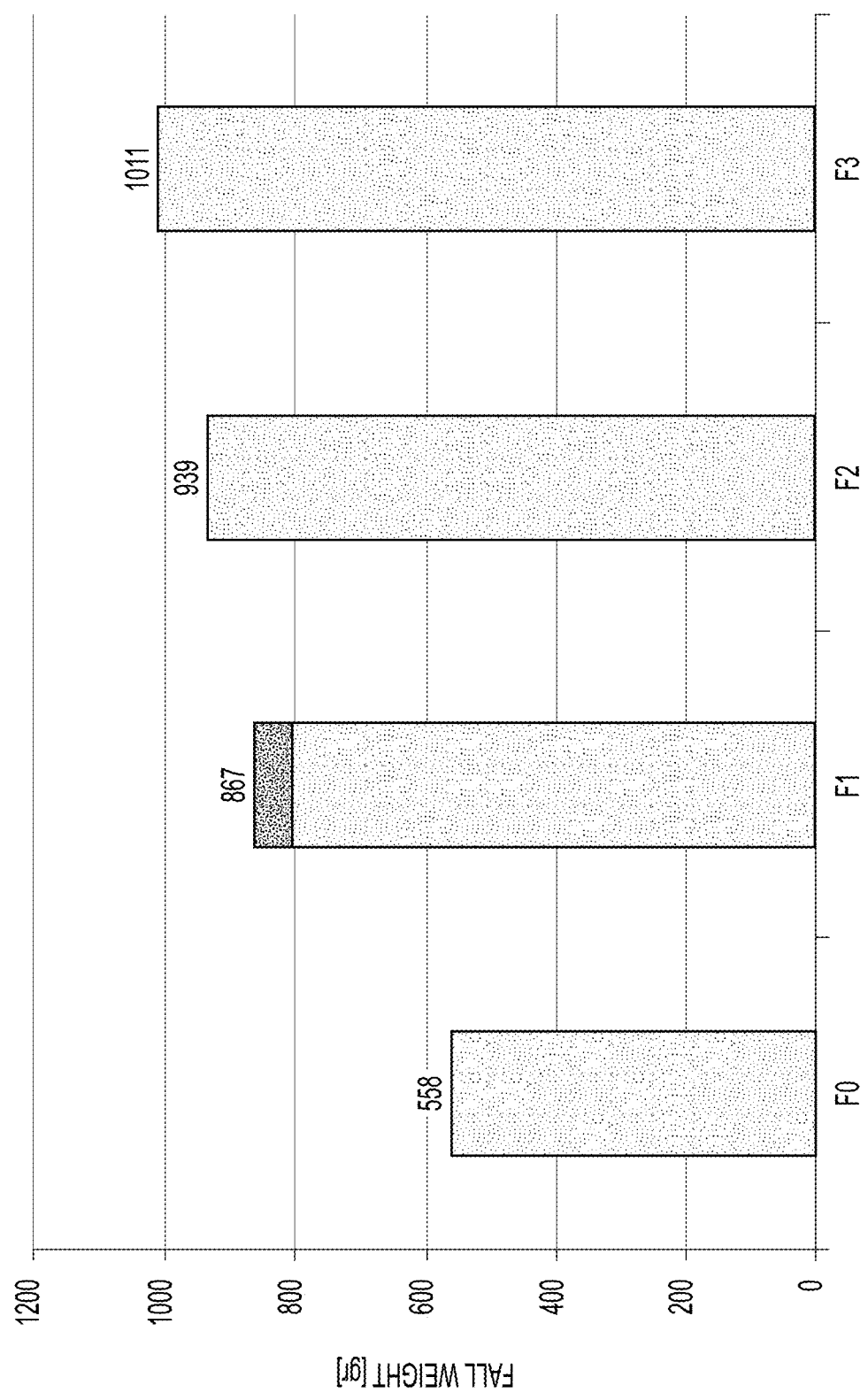
FIG. 1 demonstrates clearly that fibers and/or filaments and/or films and/or threads comprising the inventive surface treated filler material product prepared in accordance with the present invention show increased values in dart drop.
Figure 2:
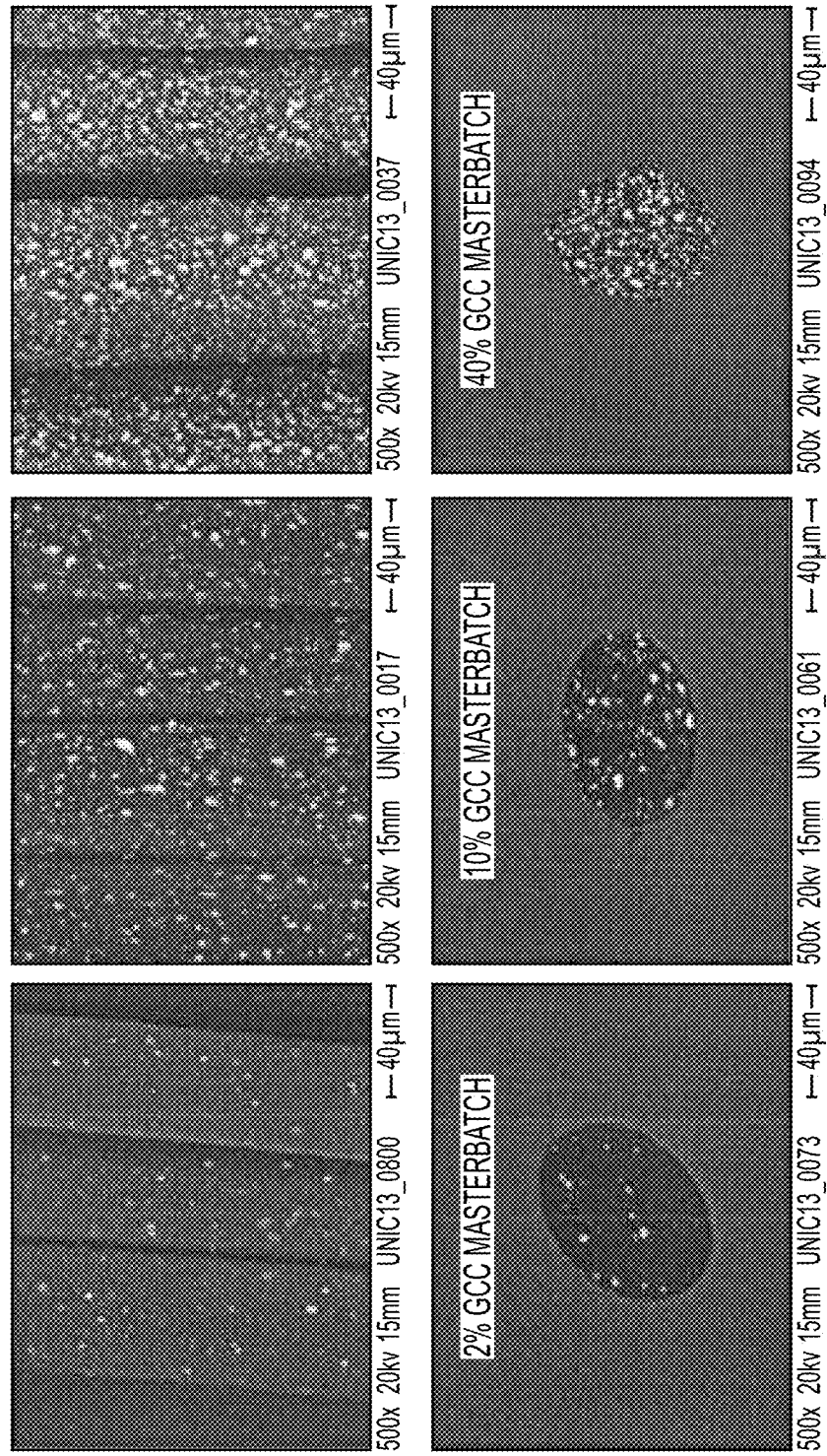
FIG. 2 shows scanning electron micrographs (SEM) of PP multifilament fibers containing calcium carbonate. Fiber surface (top) & fiber cross section (bottom), 500× magnification [40 um].

The following examples may additionally illustrate the invention but are not meant to restrict the invention to the exemplified embodiments. The examples below show the reduced total volatiles, the reduced moisture pick up susceptibility and the decreased hydrophilicity of the surface treated filler material product and the good mechanical properties of the fiber and/or filament and/or film and/or thread prepared from the polymer composition according to the present invention:

EXAMPLES

Measurement Methods

The following measurement methods are used to evaluated the parameters given in the examples and claims.

Measurement of the Total Volatiles

For the purpose of the present application, the "total volatiles" associated with mineral fillers and evolved over a temperature range of 25 to 350° C. is characterized according to % mass loss of the mineral filler sample over a temperature range as read on a thermogravimetric (TGA) curve.

TGA analytical methods provide information regarding losses of mass and volatile onset temperatures with great accuracy, and is common knowledge; it is, for example, described in "Principles of Instrumental analysis", fifth edition, Skoog, Holler, Nieman, 1998 (first edition 1992) in Chapter 31 pages 798 to 800, and in many other commonly known reference works. In the present invention, thermogravimetric analysis (TGA) is performed using a Mettler Toledo TGA 851 based on a sample of 500+/−50 mg and scanning temperatures from 25 to 350° C. at a rate of 20° C./minute under an air flow of 70 ml/min.

The skilled man will be able to determine the "volatile onset temperature" by analysis of the TGA curve as follows: the first derivative of the TGA curve is obtained and the inflection points thereon between 150 and 350° C. are identified. Of the inflection points having a tangential slope value of greater than 45° relative to a horizontal line, the one having the lowest associated temperature above 200° C. is identified. The temperature value associated with this lowest temperature inflection point of the first derivative curve is the "volatile onset temperature".

The "total volatiles" evolved on the TGA curve is determined using $Star^e$ SW 9.01 software. Using this software, the curve is first normalised relative to the original sample weight in order to obtain mass losses in % values relative to the original sample. Thereafter, the temperature range of 25 to 350° C. is selected and the step horizontal (in German: "Stufe horizontal") option selected in order to obtain the % mass loss over the selected temperature range.

Particle Size Distribution (Mass % Particles with a Diameter <X) and Weight Median Diameter ($d_{50}$) of a Particulate Material As used herein and as generally defined in the art, the "$d_{50}$" value is determined based on measurements made by using a Sedigraph™ 5100 of Micromeritics Instrument Corporation and is defined as the size at which 50% (the median point) of the particle volume or mass is accounted for by particles having a diameter equal to the specified value.

The method and the instrument are known to the skilled person and are commonly used to determine grain size of fillers and pigments. The measurement is carried out in an aqueous solution of 0.1 wt.-% $Na_4P_2O_7$. The samples are dispersed using a high speed stirrer and supersonics.

BET Specific Surface Area of a Material

Throughout the present document, the specific surface area (in $m^2/g$) of the mineral filler is determined using the BET method (using nitrogen as adsorbing gas), which is well known to the skilled man (ISO 9277:1995). The total surface area (in $m^2$) of the mineral filler is then obtained by multiplication of the specific surface area and the mass (in g) of the mineral filler prior to treatment.

Moisture Pick-Up

The term "moisture pick-up susceptibility" in the meaning of the present invention refers to the amount of moisture absorbed on the surface of the mineral filler and is determined in mg moisture/g of the dry treated mineral filler product after exposure to an atmosphere of 10 and 85% of relative humidity, resp., for 2.5 hours at a temperature of +23° C. (±2° C.). The treated mineral filler product is first held at an atmosphere of 10% of relative humidity for 2.5 hours, then the atmosphere is changed to 85% of relative humidity, where the sample is held for another 2.5 hours. The weight increase between 10% and 85% relative humidity is then used to calculate the moisture pick-up in mg moisture/g of dry treated mineral filler product.

Hydrophilicity

The "hydrophilicity" of a mineral filler product is evaluated at +23° C. by determining the minimum water to ethanol ratio in a volume/volume based water/ethanol-mixture needed for the settling of the majority of said mineral filler product, where said mineral filler product is deposited on the surface of said water/ethanol-mixture by passage through a house hold tea sieve. The volume/volume base is related to the volumes of both separate liquids before blending them together and do not include the volume contraction of the blend. The evaluation at +23° C. refers to a temperature of +23° C.±1° C.

A 8:2 volumetric ratio of a water/ethanol-mixture has typically a surface tension of 41 mN/m and a 6:4 volumetric ratio of a water/ethanol-mixture has typically a surface tension of 26 mN/m measured at +23° C. as described in the "Handbook of Chemistry and Physics", $84^{th}$ edition, David R. Lide, 2003 (first edition 1913).

Dart Drop Test

The dart drop test is measured according to ASTM D 1709/A.

Residual Total Moisture Content Measurement of Calcium Carbonate-Containing Material The residual total moisture content of the filler is measured according to the Karl Fischer coulometric titration method, desorbing the moisture in an oven at 220° C. and passing it continuously into the KF coulometer (Mettler Toledo coulometric KF Titrator C30, combined with Mettler oven DO 0337) using dry $N_2$ at 100 ml/min for 10 min. A calibration curve using water has to be made and a blind of 10 min gas flow without a sample has to be taken in account.

Measurements Done on Filament Samples

Titer or Linear density [dtex] may be measured according to EN ISO 2062 and corresponds to the weight in grams of 10'000 m yarn. A sample of 25 or 100 meters is wound up on a standard reel under a pretension of 0.5 cN/tex and weighted on an analytical scale. The grams per 10'000 m yarn length are then calculated.

Tenacity is calculated from the breaking force and the linear density, and expressed in centinewton per tex [cN/tex]. The test is carried out on a dynamometer with a constant stretching speed, applicable standards for this test are EN ISO 5079 and ASTM D 3822.

Breaking force and elongation at break: The breaking force is the force needed to be applied on a yarn to make it break. It is expressed in Newton [N]. The elongation at break is the increase of the length produced by stretching a yarn to its breaking point. It is expressed as a percentage [%] of its initial length.

Tensile index is the product of tenacity [cN/tex] and the square root of the elongation at break [%].

Measurements Done on Nonwoven Samples

Fabric weight or mass per unit area [$g/m^2$] is measured according to EN ISO 9864.

Tensile properties of geotextiles are measured according to EN ISO 10319 using a wide-width strip with 200 mm width and 100 mm length on a tensile testing machine.

Tensile strength [kN/m] and the elongation at maximum load [%] are measured in machine direction (MD) and in cross machine direction (CD). The energy value according to EN ISO 10319 is calculated by the tensile strength (MD+CD)/2.

Static puncture resistance (CBR test) in [kN] is measured according to EN ISO 12236. This method specifies the determination of the puncture resistance by measuring the force required to push a flat-ended plunger through geosynthetics.

Ash content in [%] of the fibers and the masterbatches is determined by incineration of a sample in an incineration crucible which is put into an incineration furnace at 570° C. for 2 hours. The ash content is measured as the total amount of remaining inorganic residues.

Example 1

This example relates to the preparation of a surface treated filler material product in accordance with the process of the present invention.

For the preparation of the surface treated filler material product, lime stone from Omey, France was wet ground at 25 wt.-% in tap water in a horizontal ball mill (Dynomill) and spray dried. The obtained calcium carbonate-containing filler material features a $d_{50}$ of approximately 1.7 microns, a top cut ($d_{98}$) of 5 μm and a specific surface area of 4.1 $m^2/g$ and a residual moisture content of 0.06 wt.-%.

The obtained spray dried calcium carbonate-containing filler material was further treated as outlined in the following tests:

Test 1 (Prior Art; PA1)

500 g of the spray dried calcium carbonate-containing filler material was added to an MTI Mixer and the sample was activated for 5 minutes at 180° C. and 3000 rpm. Thereafter polystyren-co-maleic anhydride having a Mn of 1600 (Aldrich number 442380) was introduced to the mixer in a quantity such as indicated in Table 1. The contents of the mixer were mixed at 180° C. under a stirring speed of 3000 rpm for a period of 5 minutes.

The obtained surface treated filler material product was stored in a closed plastic bag. For analysis purposes the sample was taken out of the closed plastic bag and analyzed immediately. The results are presented in table 2.

Test 2 (Prior Art; PA2)

500 g of the spray dried calcium carbonate-containing filler material was added to an MTI Mixer and the sample was activated for 5 minutes at 80° C. and 3000 rpm. Thereafter, 1,2-cyclohexanedicarboxylic anhydride (Aldrich number 123463) was introduced to the mixer in a quantity such as indicated in Table 1. The contents of the mixer were mixed at 80° C. under a stirring speed of 3000 rpm for a period of 5 minutes.

The obtained surface treated filler material product was stored in a closed plastic bag. For analysis purposes the sample was taken out of the closed plastic bag and analyzed immediately. The results are presented in table 2.

Test 3 (Prior Art; PA3)

500 g of the spray dried calcium carbonate-containing filler material was added to an MTI Mixer and the sample was activated for 5 minutes at 80° C. and 3000 rpm. Thereafter, phenyl succinic anhydride (Aldrich number 416622) was introduced to the mixer in a quantity such as indicated in Table 1. The contents of the mixer were mixed at 80° C. under a stirring speed of 3000 rpm for a period of 5 minutes.

The obtained surface treated filler material product was stored in a closed plastic bag. For analysis purposes the sample was taken out of the closed plastic bag and analyzed immediately. The results are presented in table 2.

Test 4 (Invention; IE4)

500 g of the spray dried calcium carbonate-containing filler material was added to an MTI Mixer and the sample was activated for 10 minutes at 120° C. and 3000 rpm. Thereafter, n-octadecenyl succinic anhydride having a purity of ≥96.5% was introduced to the mixer in a quantity such as indicated in Table 1. The contents of the mixer were mixed at 120° C. under a stirring speed of 3000 rpm for a period of 10 minutes.

The obtained surface treated filler material product was stored in a closed plastic bag. For analysis purposes the sample was taken out of the closed plastic bag and analyzed immediately. The results are presented in table 2.

Test 5 (Invention; IE5)

500 g of the spray dried calcium carbonate-containing filler material was added to an MTI Mixer and the sample was activated for 10 minutes at 120° C. and 3000 rpm. Thereafter, a mixture of branched hexadecenyl succinic anhydrides (CAS #32072-96-1) and branched octadecenyl succinic anhydrides (CAS #28777-98-2) comprising an amount of branched octadecenyl succinic anhydrides of about 40 wt.-%, based on the total weight of the succinic anhydride mixture was introduced to the mixer in a quantity such as indicated in Table 1. The contents of the mixer were mixed at 120° C. under a stirring speed of 3000 rpm for a period of 10 minutes.

The obtained surface treated filler material product was stored in a closed plastic bag. For analysis purposes the sample was taken out of the closed plastic bag and analyzed immediately. The results are presented in table 2.

Test 6 (Invention; IE6)

500 g of the spray dried calcium carbonate-containing filler material was added to an MTI Mixer and the sample was activated for 10 minutes at 120° C. and 3000 rpm. Thereafter, n-butylsuccinic anhydride (TCI Europe N.V. product number B2742) was introduced to the mixer in a quantity such as indicated in Table 1. The contents of the mixer were mixed at 120° C. under a stirring speed of 3000 rpm for a period of 10 minutes followed by the addition of 500 ppm of polydimethylsiloxane (Dow Corning 200 Fluid 1000 CS) and mixing at 3000 rpm for 5 minutes at 120° C.

The obtained surface treated filler material product was stored in a closed plastic bag. For analysis purposes the sample was taken out of the closed plastic bag and analyzed immediately. The results are presented in table 2.

Test 7 (Invention; IE7)

500 g of the spray dried calcium carbonate-containing filler material was added to an MTI Mixer and the sample was activated for 30 minutes at 120° C. and 3000 rpm. Thereafter, n-octenylsuccinic anhydride (cis and trans mixture; TCI Europe N.V. product number O0040) was introduced to the mixer in a quantity such as indicated in Table 1. The contents of the mixer were mixed at 120° C. under a stirring speed of 3000 rpm for a period of 20 minutes followed by the addition of 500 ppm of polydimethylsiloxane (Dow Corning 200 Fluid 1000 CS) and mixing at 3000 rpm for 5 minutes at 120° C.

The obtained surface treated filler material product was stored in a closed plastic bag. For analysis purposes the sample was taken out of the closed plastic bag and analyzed immediately. The results are presented in table 2.

Test 8 (Invention; IE8)

500 g of the spray dried calcium carbonate-containing filler material was added to an MTI Mixer and the sample was activated for 10 minutes at 120° C. and 3000 rpm. Thereafter, a mixture of branched hexadecenyl succinic anhydrides (CAS #32072-96-1) and branched octadecenyl succinic anhydrides (CAS #28777-98-2) comprising an amount of branched octadecenyl succinic anhydrides of about 40 wt.-%, was introduced to the mixer in a quantity such as indicated in Table 1. The contents of the mixer were mixed at 120° C. under a stirring speed of 3000 rpm for a period of 10 minutes followed by the addition of 500 ppm of polydimethylsiloxane (Dow Corning 200 Fluid 1000 CS) and mixing at 3000 rpm for 5 minutes at 120° C.

The obtained surface treated filler material product was stored in a closed plastic bag. For analysis purposes the sample was taken out of the closed plastic bag and analyzed immediately. The results are presented in table 2.

TABLE 1

| Test | PA 1 | PA 2 | PA 3 | IE 4 | IE 5 | IE 6 | IE 7 | IE 8 |
|---|---|---|---|---|---|---|---|---|
| treatment level [wt.-%] | 1.0 | 1.0 | 1.0 | 0.5 | 0.6 | 0.6* | 0.6* | 0.6* |
| preheating Time/temperature ([min]/[° C.]) | 5/180 | 5/80 | 5/80 | 10/120 | 10/120 | 10/120 | 30/120 | 5/120 |
| treatment time/temperature ([min]/[° C.]) | 5/180 | 5/80 | 5/80 | 10/120 | 10/120 | 10/120# | 20/120# | 10/180# |

*comprises an additional treatment level of 0.05 wt.-% of siloxane, based on the total weight of calcium carbonate-containing filler material.
comprises an additional treatment step with siloxane for 5 min at 120° C.

The results for the analysis of the surface treated filler material product as described above are outlined in table 2.

TABLE 2

| Test | PA 1 | PA 2 | PA 3 | IE 4 | IE 5 | IE 6 | IE 7 | IE 8 |
|---|---|---|---|---|---|---|---|---|
| Moisture pick-up [mg/g] | — | — | — | 0.31 | 0.33 | 0.21 | 0.29 | 0.27 |
| OST [° C.] | — | — | — | 278 | 283 | 335 | — | — |
| Hydrophilicity [vol/vol-%] | 100 | 100 | 100 | 60 | 60 | 60 | 70 | 50 |

From the data given in Table 2, it can be gathered that the surface treated filler material product prepared in accordance with the present invention shows excellent properties. In particular, it is shown that the surface treated filler material product prepared in accordance with the present invention has a moisture pick up susceptibility of less than 0.8 mg/g, a volatile onset temperature of ≥250° C., and a hydrophilicity of below 8:2 volumetric ratio of water:ethanol.

Example 2

This example relates to the preparation of a blown film comprising the surface treated filler material product prepared in accordance with the present invention and at least one polymeric resin.

The details regarding the blown film polymer compositions, based on the total weight of the obtained film, are described in Table 3.

TABLE 3

| Formulation | [g/cm³] | F0 | F1 | F2 | F3 |
|---|---|---|---|---|---|
| Polymer resin | 0.924 | 100 | 40 | 40 | 40 |
| Treated carbonate A | 2.7 | | 60 | | |
| IE4 | 2.7 | | | 60 | |
| IE5 | 2.7 | | | | 60 |

The polymer compositions used for preparing the blown film were afterwards diluted to 20 wt.-% calcium carbonate-containing material, based on the total weight of the obtained film.

Treated carbonate A is a stearic acid treated dry ground calcium carbonate (marble from Italy) with a medium diameter ($d_{50}$) of 1.7 μm and a top cut ($d_{98}$) of 6.8 μm. 57 wt.-% of the particles have a diameter of below 2 μm. This treated filler material is used as an internal reference.

Polymer resin relates to a linear low density polyethylene resin (LLDPE) which is commercially available as Dowlex NG 5056G from Dow Chemical Company, Dow Europe GmbH, Horgen, Switzerland.

Polymer composition F0 contains only the pure polymer resin, no surface treated filler material product is included.

The blown film was prepared on a Collin blown film line with a film grammage of 37.5 g/m² and a film thickness of 40 μm.

The fiber and/or filament and/or film and/or thread comprising the inventive surface treated filler material product prepared in accordance with the present invention show excellent mechanical properties such as shown in FIG. 1.

FIG. 1 demonstrates clearly that fibers and/or filaments and/or films and/or threads comprising the inventive surface treated filler material product prepared in accordance with the present invention show increased values in dart drop. In particular, it is shown that the values determined for the dart drop of the fibers and/or filaments and/or films and/or threads comprising the inventive surface treated filler material product prepared in accordance with the present invention are significantly higher than the values determined for the sample consisting only of the polymeric resin as well as for the reference sample.

It is further appreciated that the polymer composition comprising the inventive surface treated filler material product prepared in accordance with the present invention and which is used for preparing the fiber and/or filament and/or film and/or thread also shows an excellent filter pressure value (FPV) as can be gathered from Table 4.

TABLE 4

| Sample | FPV, 16 g GCC, 14 μm screen [bar/g] |
|---|---|
| F1 | 1.8 |
| F2 | 0.7 |
| F3 | 0.8 |

Example 3

This example relates to the preparation of a nonwoven fabric comprising the surface treated filler material product prepared in accordance with the present invention and at least one polymeric resin.

Samples of the said nonwoven fabrics comprising the $CaCO_3$ according to the present invention and samples of nonwoven fabrics comprising the prior art $CaCO_3$ are compared hereafter in tables 5 and 6. Different amounts of the filled masterbatches were mixed with further polypropylene (PP HF420FB, a homo-polypropylene with MFR 19 g/10 min. (230° C., 2.16 kg, ISO 1133) from *Borealis*) and nonwoven fabrics were made from these mixtures.

TABLE 5

| Formulation | | | 1 | 2 | 3 | 4 |
|---|---|---|---|---|---|---|
| Polypropylene HF420FB | | | 100 | 96 | 96 | 96 |
| 70% MB Invention 1 | | | | 4 | | |
| 70% MB Invention 2 | | | | | 4 | |
| 70% MB Prior Art 1 | | | | | | 4 |
| Tests | Norm | Unit | | | | |
| *On Filaments* | | | | | | |
| Linear density | | dtex | 9.3 | 10.1 | 9.3 | 9.7 |
| Tenacity | | cN/dtex | 2.26 | 2.08 | 2.03 | 2.09 |
| Elongation | | % | 252 | 251 | 239 | 229 |
| Tensile index | | — | 359 | 330 | 314 | 316 |
| *On Nonwoven* | | | | | | |
| Fabric weight | EN ISO 9864 | g/m² | 372 | 388 | 367 | 387 |
| Coefficient CBR | EN ISO12236 | N/g | 7.5 | 5.9 | 6.7 | 7.1 |
| CBR | EN ISO12236 | N | 2766 | 2271 | 2449 | 2741 |
| Tensile Strength (MD + CD)/2 | EN ISO 12319 | N/g | 10.6 | 9.5 | 10.2 | 9.3 |
| Ash content | | % | 0 | 2.4 | 2.5 | 3.0 |

[1] MD refers to machine direction,
[2] CD refers to cross direction.

TABLE 6

| Formulation | | | 1 | 2 | 3 | 4 |
|---|---|---|---|---|---|---|
| Polypropylene HF420FB | | | 100 | 90 | 90 | 90 |
| 70% MB Invention1 | | | | 10 | | |
| 70% MB Invention 2 | | | | | 10 | |
| 70% MB Prior Art 1 | | | | | | 10 |
| Tests | Norm | Unit | | | | |
| *On Filaments* | | | | | | |
| Linear density | | dtex | 9.3 | 10.4 | 10.0 | 10.0 |
| Tenacity | | cN/dtex | 2.26 | 1.97 | 1.99 | 1.87 |
| Elongation | | % | 252 | 244 | 239 | 226 |
| Tensile index | | — | 359 | 308 | 308 | 281 |
| *On Nonwoven* | | | | | | |
| Fabric weight | EN ISO 9864 | g/m² | 372 | 405 | 385 | 401 |
| Coefficient CBR | EN ISO12236 | N/g | 7.5 | 6.2 | 5.6 | 6.2 |
| CBR | EN ISO12236 | N | 2766 | 2522 | 2142 | 2479 |
| Tensile Strength (MD + CD)/2 | EN ISO 12319 | N/g | 10.6 | 8.3 | 8.3 | 7.6 |
| Ash content | | % | 0 | 5.9 | 5.9 | 7.0 |

[1] MD refers to machine direction,
[2] CD refers to cross direction

70% MB Invention 1 refers to 70 wt % of a masterbatch of 28 wt % PP HH450 FB homo-polypropylene with MFR 37 g/10 min. (230° C., 2.16 kg, ISO 1133) from *Borealis* and 2 wt % Irgastab FS 301, processing and thermal stabilizer from BASF and 70 wt % of $CaCO_3$ according to the present invention, wherein the treated $CaCO_3$ has a median particles size diameter d50 of 1.7 μm, a top cut of d98 of 6 μm. Treatment of the $CaCO_3$: 0.5 wt % of Hydrores AS 1000 (KEMIRA; CAS number 68784-12-3): 500 g of the spray dried calcium carbonate-containing filler material was added to an MTI Mixer and the sample was activated for 10 minutes at 120° C. and 3000 rpm. Thereafter, Hydrores AS 1000 (Kemira) was introduced to the mixer in a quantity of 0.5 wt %. The contents of the mixer were mixed at 120° C. under a stirring speed of 3000 rpm for a period of 10 minutes.

The obtained surface treated filler material product was stored in a closed plastic bag. For analysis purposes the sample was taken out of the closed plastic bag and analyzed immediately. T onset: 289° C.; Water-pick-up: 0.7 mg/g 70% MB Invention 2 refers to 70 wt % of a masterbatch of 28 wt % PP HH450 FB homo-polypropylene with MFR 37 g/10 min. (230° C., 2.16 kg, ISO 1133) from *Borealis* and 2 wt % Irgastab FS 301, processing and thermal stabilizer from BASF and 70 wt % of $CaCO_3$ according to the present invention, wherein the treated $CaCO_3$ has a median particles size diameter d50 of 1.7 μm, a top cut of d98 of 6 μm. Treatment of the $CaCO_3$: 0.6 wt % Hydrores AS 1100 (KEMIRA, CAS number 68784-12-3):

500 g of the spray dried calcium carbonate-containing filler material was added to an MTI Mixer and the sample was activated for 10 minutes at 120° C. and 3000 rpm. Thereafter, Hydrores AS 1100 (Kemira) was introduced to the mixer in a quantity a quantity of 0.6 wt %. The contents of the mixer were mixed at 120° C. under a stirring speed of 3000 rpm for a period of 10 minutes.

The obtained surface treated filler material product was stored in a closed plastic bag. For analysis purposes the sample was taken out of the closed plastic bag and analyzed immediately. T onset: 300° C.; Water-pick-up: 0.8 mg/g 70% of MA PA1 refers to 70 wt % of a masterbatch of 28 wt % PP HH450 FB homo-polypropylene with MFR 37 g/10 min. (230° C., 2.16 kg, ISO 1133) from *Borealis* and 2 wt % Irgastab FS 301, processing and thermal stabilizer from BASF and 70 wt % of a wet ground surface treated $CaCO_3$ of the prior art, and the $CaCO_3$ has a median particle size diameter d50 of 1.7 μm and a top cut of d98 of 6 μm.

As can be seen from the inventive examples 2 and 3 from tables 5 and 6, samples of polypropylene nonwoven fabrics comprises the $CaCO_3$ according to the present invention and as seen in example 4 from tables 5 and 6, samples of nonwoven fabrics comprising the prior art $CaCO_3$ can be produced in good quality with slightly reduced mechanical properties compared to Example 1 being the unfilled polypropylene PP HF420FB.

It lies within the scope of the present invention that the polypropylenes mentioned are not the only one and that other PP polymers or PE polymers or a mix of PP and PE polymers are suitable as well to be used for producing a masterbatch comprising the $CaCO_3$ of the present invention.

Example 4

This example relates to the preparation of multifilament fibers comprising the surface treated filler material product prepared in accordance with the present invention and at least one polymeric resin.

Samples of the said multifilament fibers comprising the $CaCO_3$ according to the present invention and samples of multifilament fibers comprising the prior art $CaCO_3$ are summarized hereafter in tables 8 to 14. Different amounts of the filled masterbatches were mixed with further polypropylene (Moplen HP 561R, a homo-polypropylene with MFR 25 g/10 min. (230° C., 2.16 kg, ISO 1133) from Lyondell-Basell) and multifilament fibers were made from these mixtures using a Collin Multifilament Lab Line CMF 100 (produced by Dr. Collin GmbH, Ebersberg, Germany), equipped with a single screw extruder with melt pump, spinneret diameter 50 mm with 34 filaments Ø 0.3 mm, Drawing conditions are summarized in table 7. Limanol BF29 (from Schill+Seilacher GmbH, Böblingen, Germany) is used as spinning oil.

TABLE 7

| Drawing temperatures: | | | |
|---|---|---|---|
| | Condition 1 | Condition 2 | Condition 3 |
| Roll 1 | 80° C. | 100° C. | 110° C. |
| Roll 2 | 85° C. | 105° C. | 115° C. |
| Roll 3 | 90° C. | 105° C. | 115° C. |
| Roll 4 | 90° C. | 110° C. | 120° C. |

TABLE 8

| | Inventive masterbatch | | | | | | |
|---|---|---|---|---|---|---|---|
| Example | Masterbatch | Draw temp. condition | Draw ratio | Tenacity [cN/dtex] | Elongation at max. load [%] | Linear density [dtex] | Ash content [%] |
| 1 | 2% MB Inv. 3 | 1 | 2 | 1.23 | 223 | 754 | 1.3 |
| 2 | 5% MB Inv. 3 | 1 | 2 | 1.01 | 221 | 796 | 10.8 |
| 3 | 10% MB Inv. 3 | 1 | 2 | 1.14 | 171 | 742 | 9.7 |
| 4 | 15% MB Inv. 3 | 1 | 2 | 1.05 | 202 | 848 | 14.2 |
| 5 | 20% MB Inv. 3 | 1 | 2 | 0.76 | 215 | 904 | 23.1 |
| 6 | 25% MB Inv. 3 | 1 | 2 | 0.73 | 180 | 962 | 28.0 |
| 7 | 30% MB Inv. 3 | 1 | 2 | 0.57 | 218 | 1012 | 30.6 |
| 8 | 40% MB Inv. 3 | 1 | 2 | 0.53 | 201 | 1042 | 38.9 |
| 9 | 10% MB Inv. 3 | 1 | 3 | 1.51 | 134 | 554 | 8.1 |
| 10 | 10% MB Inv. 3 | 1 | 4 | 1.94 | 81 | 434 | 9.5 |
| 11 | 10% MB Inv. 3 | 1 | 5 | 2.35 | 38 | 355 | 10.9 |
| 12 | 10% MB Inv. 3 | 1 | 6 | 2.82 | 15 | 310 | 10.7 |
| 13 | 15% MB Inv. 3 | 1 | 3 | 0.89 | 99 | 578 | 17.0 |
| 14 | 15% MB Inv. 3 | 1 | 4 | 1.33 | 94 | 425 | 17.0 |

TABLE 8-continued

Inventive masterbatch

| Example | Masterbatch | Draw temp. condition | Draw ratio | Tenacity [cN/dtex] | Elongation at max. load [%] | Linear density [dtex] | Ash content [%] |
|---|---|---|---|---|---|---|---|
| 15 | 15% MB Inv. 3 | 1 | 5 | 1.74 | 76 | 350 | 16.5 |
| 16 | 15% MB Inv. 3 | 1 | 6 | 1.79 | 60 | 309 | 17.1 |
| 17 | 20% MB Inv. 3 | 1 | 3 | 0.84 | 105 | 610 | 22.9 |
| 18 | 20% MB Inv. 3 | 1 | 4 | 1.09 | 111 | 449 | 19.8 |
| 19 | 20% MB Inv. 3 | 1 | 5 | 1.34 | 93 | 350 | 21.6 |
| 20 | 20% MB Inv. 3 | 1 | 6 | 1.78 | 58 | 293 | 19.4 |

TABLE 9

Inventive masterbatch

| Example | Masterbatch | Draw temp. condition | Draw ratio | Tenacity [cN/dtex] | Elongation at max. load [%] | Linear density [dtex] | Ash content [%] |
|---|---|---|---|---|---|---|---|
| 21 | 10% MB Inv. 3 | 2 | 2 | 0.54 | 219 | 792 | 9.7 |
| 22 | 10% MB Inv. 3 | 2 | 3 | 0.89 | 183 | 519 | 10.2 |
| 23 | 10% MB Inv. 3 | 2 | 4 | 1.25 | 107 | 426 | 11.3 |
| 24 | 10% MB Inv. 3 | 2 | 5 | 1.71 | 77 | 350 | 12.7 |
| 25 | 15% MB Inv. 3 | 2 | 2 | 0.5 | 207 | 822 | 16.6 |
| 26 | 15% MB Inv. 3 | 2 | 3 | 0.79 | 152 | 560 | 18.2 |
| 27 | 15% MB Inv. 3 | 2 | 4 | 1.35 | 73 | 428 | 17.2 |
| 28 | 15% MB Inv. 3 | 2 | 5 | 1.9 | 74 | 359 | 16.1 |
| 29 | 20% MB Inv. 3 | 2 | 2 | 0.51 | 217 | 868 | 20.9 |
| 30 | 20% MB Inv. 3 | 2 | 3 | 0.89 | 193 | 561 | 21.1 |
| 31 | 20% MB Inv. 3 | 2 | 4 | 1.17 | 112 | 451 | 22.8 |
| 32 | 20% MB Inv. 3 | 2 | 5 | 1.4 | 84 | 362 | 17.8 |

TABLE 10

Inventive masterbatch

| Example | Masterbatch | Draw temp. condition | Draw ratio | Tenacity [cN/dtex] | Elongation at max. load [%] | Linear density [dtex] | Ash content [%] |
|---|---|---|---|---|---|---|---|
| 33 | 10% MB Inv. 3 | 3 | 2 | 0.91 | 196 | 678 | 10.5 |
| 34 | 10% MB Inv. 3 | 3 | 3 | 1.17 | 126 | 499 | 10.3 |
| 35 | 10% MB Inv. 3 | 3 | 4 | 1.2 | 104 | 390 | 9.5 |
| 36 | 10% MB Inv. 3 | 3 | 5 | 1.92 | 66 | 335 | 8.3 |
| 37 | 15% MB Inv. 3 | 3 | 2 | 0.89 | 170 | 679 | 12.0 |
| 38 | 15% MB Inv. 3 | 3 | 3 | 1.08 | 146 | 499 | 14.3 |
| 39 | 15% MB Inv. 3 | 3 | 4 | 1.73 | 97 | 402 | 15.5 |
| 40 | 15% MB Inv. 3 | 3 | 5 | 1.82 | 19 | 362 | 16.0 |
| 41 | 20% MB Inv. 3 | 3 | 2 | 0.72 | 183 | 846 | 21.2 |
| 42 | 20% MB Inv. 3 | 3 | 3 | 1.11 | 117 | 572 | 21.1 |
| 43 | 20% MB Inv. 3 | 3 | 4 | 1.34 | 71 | 427 | 20.5 |
| 44 | 20% MB Inv. 3 | 3 | 5 | 1.66 | 66 | 348 | 19.2 |

TABLE 11

Prior art masterbatch

| Example | Masterbatch | Draw temp. condition | Draw ratio | Tenacity [cN/dtex] | Elongation at max. load [%] | Linear density [dtex] | Ash content [%] |
|---|---|---|---|---|---|---|---|
| 45 | 2% MB PA2 | 1 | 2 | 1.36 | 223 | 736 | 1.8 |
| 46 | 5% MB PA2 | 1 | 2 | 0.95 | 222 | 774 | 4.6 |
| 47 | 10% MB PA2 | 1 | 2 | 0.94 | 169 | 623 | 12.1 |
| 48 | 20% MB PA2 | 1 | 2 | 0.78 | 205 | 555 | 21.2 |

TABLE 11-continued

| | | Prior art masterbatch | | | | | |
|---|---|---|---|---|---|---|---|
| Example | Masterbatch | Draw temp. condition | Draw ratio | Tenacity [cN/dtex] | Elongation at max. load [%] | Linear density [dtex] | Ash content [%] |
| 49 | 10% MB PA2 | 1 | 3 | 1.61 | 144 | 533 | 4.9 |
| 50 | 10% MB PA2 | 1 | 4 | 2.09 | 70 | 386 | 2.4 |
| 51 | 10% MB PA2 | 1 | 5 | 2.56 | 59 | 338 | 8.9 |
| 52 | 10% MB PA2 | 1 | 6 | 2.97 | 14 | 287 | 10.3 |
| 53 | 15% MB PA2 | 1 | 3 | 1.83 | 124 | 597 | 17.0 |
| 54 | 15% MB PA2 | 1 | 4 | 1.88 | 73 | 458 | 17.0 |
| 55 | 15% MB PA2 | 1 | 5 | 2.35 | 38 | 366 | 14.3 |
| 56 | 15% MB PA2 | 1 | 6 | 3.17 | 16 | 306 | 14.3 |
| 57 | 20% MB PA2 | 1 | 3 | 1.29 | 116 | 606 | 20.1 |
| 58 | 20% MB PA2 | 1 | 4 | 1.51 | 63 | 465 | 20.7 |
| 59 | 20% MB PA2 | 1 | 5 | 2.11 | 32 | 378 | 19.2 |
| 60 | 20% MB PA2 | 1 | 6 | 2.36 | 13 | 339 | 22.5 |

TABLE 12

| | | Prior art masterbatch | | | | | |
|---|---|---|---|---|---|---|---|
| Example | Masterbatch | Draw temp. condition | Draw ratio | Tenacity [cN/dtex] | Elongation at max. load [%] | Linear density [dtex] | Ash content [%] |
| 61 | 10% MB PA2 | 2 | 2 | 0.48 | 219 | 820 | 10.1 |
| 62 | 10% MB PA2 | 2 | 3 | 1.36 | 109 | 539 | 10.8 |
| 63 | 10% MB PA2 | 2 | 4 | 1.69 | 83 | 414 | 8.7 |
| 64 | 10% MB PA2 | 2 | 5 | 2.11 | 77 | 319 | 8.7 |
| 65 | 15% MB PA2 | 2 | 2 | 0.55 | 219 | 861 | 19.9 |
| 66 | 15% MB PA2 | 2 | 3 | 0.71 | 89 | 587 | 17.6 |
| 67 | 15% MB PA2 | 2 | 4 | 1.66 | 95 | 424 | 15.9 |
| 68 | 15% MB PA2 | 2 | 5 | 1.74 | 77 | 351 | 14.6 |
| 69 | 20% MB PA2 | 2 | 2 | 0.68 | 214 | 870 | 18.8 |
| 70 | 20% MB PA2 | 2 | 3 | 0.9 | 89 | 588 | 15.8 |
| 71 | 20% MB PA2 | 2 | 4 | 1.51 | 69 | 432 | 16.2 |
| 72 | 20% MB PA2 | 2 | 5 | 1.72 | 47 | 354 | 15.6 |

TABLE 13

| | | Prior art masterbatch | | | | | |
|---|---|---|---|---|---|---|---|
| Example | Masterbatch | Draw temp. condition | Draw ratio | Tenacity [cN/dtex] | Elongation at max. load [%] | Linear density [dtex] | Ash content [%] |
| 73 | 10% MB PA2 | 3 | 2 | 0.74 | 206 | 786 | 9.8 |
| 74 | 10% MB PA2 | 3 | 3 | 1.46 | 72 | 529 | 7.7 |
| 75 | 10% MB PA2 | 3 | 4 | 1.96 | 85 | 406 | 6.7 |
| 76 | 10% MB PA2 | 3 | 5 | 2.2 | 17 | 326 | 8.5 |
| 77 | 15% MB PA2 | 3 | 2 | 0.63 | 197 | 819 | 13.6 |
| 78 | 15% MB PA2 | 3 | 3 | 0.99 | 145 | 550 | 11.2 |
| 79 | 15% MB PA2 | 3 | 4 | 1.42 | 63 | 438 | 12.2 |
| 80 | 15% MB PA2 | 3 | 5 | 2.27 | 18 | 340 | 12.1 |
| 81 | 20% MB PA2 | 3 | 2 | 0.54 | 147 | 898 | 24.2 |
| 82 | 20% MB PA2 | 3 | 3 | 0.99 | 100 | 598 | 19.8 |
| 83 | 20% MB PA2 | 3 | 4 | 1.36 | 74 | 459 | 18.6 |
| 84 | 20% MB PA2 | 3 | 5 | 2.11 | 15 | 361 | 16.8 |

TABLE 14

| | | | neat polymer without masterbatch | | | |
|---|---|---|---|---|---|---|
| Example | Masterbatch | Draw temp. condition | Draw ratio | Tenacity [cN/dtex] | Elongation at max. load [%] | Linear density [dtex] | Ash content [%] |
| 85 | None | 1 | 2 | 1.34 | 210 | 732 | 0 |
| 86 | None | 1 | 3 | 1.99 | 151 | 530 | 0 |
| 87 | None | 1 | 4 | 2.56 | 92 | 409 | 0 |
| 88 | None | 1 | 5 | 2.66 | 49 | 356 | 0 |
| 89 | None | 1 | 6 | 3.57 | 15 | 286 | 0 |
| 90 | None | 1 | 7 | 4.03 | 15 | 234 | 0 |

70% MB Invention 3 refers to 70 wt % of a masterbatch produced on industrial scale wherein the treated CaCO$_3$ has a median particles size diameter d50 of 1.7 µm, a top cut of d98 of 6 µm. Treatment of the CaCO$_3$: 0.5 wt % of Hydrores AS 1000 (KEMIRA; CAS number 68784-12-3). The precise filler content of the masterbatch was determined by the ash content: 72.2 wt % and the melt flow rate (MFR, 230° C., 2.16 kg, ISO 1133) of the masterbatch is 9.13 g/10 min.

70% of MB PA2 refers to a masterbatch produced on industrial scale wherein 70 wt % of a wet ground surface treated CaCO$_3$ of the prior art is used and the CaCO$_3$ has a median particle size diameter d50 of 1.7 µm and a top cut of d98 of 6 µm. The precise filler content of the masterbatch was determined by the ash content: 72.2 wt % and the melt flow rate (MFR, 230° C., 2.16 kg, ISO 1133) of the masterbatch is 9.04 g/10 min.

As can be seen in tables 8 to 10, samples of polypropylene multifilament fibers comprises the CaCO$_3$ according to the present invention and as seen in tables 11 to 13, samples of polypropylene multifilament fibers comprising the prior art CaCO$_3$ can be produced in good quality under various processing conditions by varying the amount of CaCO$_3$ addition, the draw ratio and the draw temperatures. Table 14 shows the results of polypropylene multifilament fibers comprising no CaCO$_3$.

The invention claimed is:

1. A surface treated filler material product comprising
a) at least one calcium carbonate-containing filler material having
i) a weight median particle size d$_{50}$ value in the range from 0.1 µm to 7 µm,
ii) a top cut (d$_{98}$)≤15 µm,
iii) a specific surface area (BET) of from 0.5 to 150 m$^2$/g as measured by the BET nitrogen method, and
iv) a residual total moisture content of ≤1 wt.-%, based on the total dry weight of the at least one calcium carbonate-containing filler material, and
b) a treatment layer on the surface of the at least one calcium carbonate-containing filler material comprising (A) at least one mono-substituted succinic anhydride, (B) at least one mono-substituted succinic acid, and (C) optionally salty reaction product(s) of the at least one mono-substituted succinic acid and/or the at least one monosubstituted succinic anhydride,
wherein the surface treated filler material product comprises the treatment layer in an amount of from 0.1 to 3 wt.-%, based on the total dry weight of the at least one calcium carbonate-containing filler material.

2. The surface treated filler material product according to claim 1, wherein the molar ratio of the at least one mono-substituted succinic anhydride and the at least one mono-substituted succinic acid to the salty reaction product(s) thereof is from 99.9:0.1 to 0.1:99.9.

3. The surface treated filler material product according to claim 1, wherein the salty reaction product(s) of the at least one mono-substituted succinic acid and/or the at least one mono-substituted succinic anhydride are one or more calcium and/or magnesium salts thereof.

4. The surface treated filler material product according to claim 1, wherein the treatment layer further comprises at least one organic material.

5. The surface treated filler material product according to claim 1, wherein the surface treated filler material product comprises the treatment layer in an amount of from 0.1 to 2.5 wt.-%, based on the total dry weight of the at least one calcium carbonate-containing filler material.

6. A polymer composition comprising at least one polymeric resin and from 1 to 85 wt.-%, based on the total weight of the polymer composition, of a surface treated filler material product as defined in claim 1.

7. The polymer composition according to claim 6, wherein the at least one polymeric resin is at least one thermoplastic polymer.

8. The polymer composition according to claim 6, wherein the polymer composition is a masterbatch.

9. A fiber and/or filament and/or film and/or thread comprising a surface treated filler material product according to claim 1 and/or a polymer composition comprising the surface treated filler material product.

10. An article comprising a surface treated filler material product according to claim 1 and/or a polymer composition comprising the surface treated filler material product and/or a fiber and/or filament and/or film and/or thread comprising the surface treated filler material product, wherein the article is hygiene products, medical and healthcare products, filter products, geotextile products, agriculture and horticulture products, clothing, footwear and baggage products, household and industrial products, packaging products, or construction products.

11. The surface treated filler material product according to claim 1, wherein the at least one calcium carbonate-containing filler material is selected from ground calcium carbonate (GCC), precipitated calcium carbonate (PCC), modified calcium carbonate (MCC) and mixtures thereof.

12. The surface treated filler material product according to claim 1, wherein the at least one calcium carbonate-containing filler material comprises at least one ground calcium carbonate (GCC) selected from the group consisting of marble, chalk, dolomite, limestone and mixtures thereof and/or at least one precipitated calcium carbonate (PCC) selected from the group consisting of one or more of the aragonitic, vateritic and calcitic mineralogical crystal forms and/or at least one modified calcium carbonate (MCC).

13. The surface treated filler material product according to claim 1, wherein the at least one calcium carbonate-containing filler material has a weight median particle size $d_{50}$ from 0.25 μm to 5 μm.

14. The surface treated filler material product according to claim 1, wherein the at least one calcium carbonate-containing filler material has a top cut $(d_{98}) \geq 12.5$ μm.

15. The surface treated filler material product according to claim 1, wherein the at least one calcium carbonate-containing filler material has a specific surface area (BET) of from 0.5 to 50 m²/g as measured by the BET nitrogen method.

16. The surface treated filler material product according to claim 1, wherein the at least one calcium carbonate-containing filler material has a residual total moisture content of from 0.01 to 1.0 wt.-%, based on the total dry weight of the at least one calcium carbonate-containing filler material.

17. The surface treated filler material product according to claim 1, wherein the at least one mono-substituted succinic anhydride consists of succinic anhydride mono-substituted with a group selected from a linear, branched, aliphatic and cyclic group having a total amount of carbon atoms from C2 to C30 in the substituent.

18. The surface treated filler material product according to claim 1, wherein the at least one mono-substituted succinic anhydride is at least one alkyl mono-substituted succinic anhydride, ethylsuccinic anhydride, propylsuccinic anhydride, butylsuccinic anhydride, triisobutyl succinic anhydride, pentylsuccinic anhydride, hexylsuccinic anhydride, heptylsuccinic anhydride, octylsuccinic anhydride, nonylsuccinic anhydride, decyl succinic anhydride, dodecyl succinic anhydride, hexadecanyl succinic anhydride, octadecanyl succinic anhydride, or mixtures thereof.

19. The surface treated filler material product according to claim 1, wherein the at least one mono-substituted succinic anhydride is at least one alkenyl mono-substituted succinic anhydride, ethenylsuccinic anhydride, propenylsuccinic anhydride, butenylsuccinic anhydride, triisobutenyl succinic anhydride, pentenylsuccinic anhydride, hexenylsuccinic anhydride, heptenylsuccinic anhydride, octenylsuccinic anhydride, nonenylsuccinic anhydride, decenyl succinic anhydride, dodecenyl succinic anhydride, hexadecenyl succinic anhydride, octadecenyl succinic anhydride, or mixtures thereof.

20. The surface treated filler material product according to claim 1, wherein the salty reaction product(s) of the at least one mono-substituted succinic acid and/or the at least one mono-substituted succinic anhydride on the surface of the at least one calcium carbonate-containing filler material are one or more calcium salts and/or one or more magnesium salts thereof.

21. The surface treated filler material product according to claim 1, wherein the surface treated filler material product has a water pick-up of from 0.1 to 0.8 mg/g at a temperature of 23° C. (±2° C.).

22. The surface treated filler material product according to claim 1, wherein the surface treated filler material product has a volatile onset temperature of $\geq 250°$ C.

23. The surface treated filler material product according to claim 1, wherein the surface treated filler material product has a hydrophilicity of below 8:2 volumetric ratio of water:ethanol measured at +23° C. (±2° C.) with the sedimentation method.

24. The surface treated filler material product according to claim 1, wherein the treatment layer on the surface of the at least one calcium carbonate-containing filler material comprises at least one mono-substituted succinic anhydride, at least one mono-substituted succinic acid, and salty reaction product(s) thereof.

25. A process for preparing a surface treated filler material product of claim 1, the process comprising at least the steps of:
a) providing at least one calcium carbonate-containing filler material having
i) a weight median particle size $d_{50}$ value in the range from 0.1 μm to 7 μm,
ii) a top cut $(d_{98})$ of $\leq 15$ μm,
iii) a specific surface area (BET) of from 0.5 to 150 m²/g as measured by the BET nitrogen method, and
iv) a residual total moisture content of $\leq 1$ wt.-%, based on the total dry weight of the at least one calcium carbonate-containing filler material,
b) providing at least one mono-substituted succinic anhydride and optionally at least one mono-substituted succinic acid in an amount of from 0.1 to 3 wt.-%, based on the total dry weight of the at least one calcium carbonate-containing filler material of step a),
c) contacting the surface of the at least one calcium carbonate-containing filler material of step a) under mixing, in one or more steps, with the at least one mono-substituted succinic anhydride and the at least one mono-substituted succinic acid of step b) such that a treatment layer comprising (A) the at least one mono-substituted succinic anhydride, (B) the at least one mono-substituted succinic acid, and (C) optionally salty reaction product(s) of the at least one mono-substituted succinic acid and/or the at least one mono-substituted succinic anhydride, is formed on the surface of said at least one calcium carbonate-containing filler material of step a),
wherein the temperature before and/or during contacting step c) is adjusted such that the temperature is at least 2° C. above the melting point of the at least one mono-substituted succinic anhydride and the at least one mono-substituted succinic acid.

26. The process according to claim 25, wherein the at least one calcium carbonate-containing filler material of step a) is preheated before contacting step c) is carried out.

27. The process according to claim 25, wherein the at least one mono-substituted succinic anhydride and the at least one mono-substituted succinic acid of step b) are provided in a total amount of from 0.1 to 2.5 wt.-%, based on the total dry weight of the at least one calcium carbonate-containing filler material.

28. The process according to claim 25, wherein the at least one mono-substituted succinic anhydride and the at least one mono-substituted succinic acid of step b) are added in contacting step c) in a total amount of from 0.1 to 2 wt.-%, based on the total dry weight of the at least one calcium carbonate-containing filler material of step a).

29. The process according to claim 25, wherein the at least one mono-substituted succinic acid of step b) is present in an amount of $\leq 10$ mol.-%, based on the molar sum of the at least one mono-substituted succinic anhydride and the at least one mono-substituted succinic acid.

30. The process according to claim 25, wherein contacting step c) is carried out at a temperature of from 30 to 200° C.

31. The process according to claim 25, wherein contacting step c) is carried out in a batch or continuous process.

32. The process according to claim 31, wherein the contacting step c) is a continuous process and comprises one or several contacting steps and the total contacting time is from 0.1 to 20 s.

33. The process according to claim 25, wherein the process further comprises step d) of contacting the at least one calcium carbonate-containing filler material of step a), in one or more steps, with at least one organic material.

34. The process according to claim 33, wherein contacting step d) is carried out during and/or after contacting step c).

35. The process according to claim 33, wherein contacting step d) is carried out at a temperature of from 40 to 200° C.

36. The process according to claim 33, wherein the at least one organic material is added in contacting step d) in an amount of from 100 to 1,000 ppm, based on the total dry weight of the at least one calcium carbonate-containing filler material of step a).

* * * * *